US007282343B1

(12) United States Patent
Abrams et al.

(10) Patent No.: US 7,282,343 B1
(45) Date of Patent: Oct. 16, 2007

(54) **COMPOSITIONS, METHODS AND KITS FOR DIAGNOSIS AND TREATMENT OF *CHLAMYDIA PNEUMONIAE* INFECTIONS OF THE SKIN AND THOSE ASSOCIATED WITH CUTANEOUS T-CELL LYMPHOMA**

(75) Inventors: J. Todd Abrams, Merion, PA (US); Brian J. Balin, Paoli, PA (US)

(73) Assignee: Intracell, LLC, Merion, PA (US)

( * ) Notice: Subject to any disclaimer, the term of this patent is extended or adjusted under 35 U.S.C. 154(b) by 779 days.

(21) Appl. No.: 10/001,067

(22) Filed: Oct. 24, 2001

Related U.S. Application Data

(60) Provisional application No. 60/242,907, filed on Oct. 24, 2000.

(51) Int. Cl.
*G01N 33/567* (2006.01)
*A61K 49/00* (2006.01)
*A61K 39/00* (2006.01)

(52) U.S. Cl. .................. 435/7.21; 435/7.2; 424/9.1; 424/184.1; 436/501

(58) Field of Classification Search ................ 435/7.2, 435/7.36, 69.1, 69.3, 69.7, 69.8, 71.1, 91.1, 435/91.4, 252.3, 320.1, 340, 7.21; 424/184.1, 424/185.1, 263.1, 9.1; 514/2, 44; 530/350, 530/388.4, 389.5, 412, 825; 536/23.1, 23.7, 536/24.1, 24.2, 24.3, 24.32; 436/501
See application file for complete search history.

(56) References Cited

U.S. PATENT DOCUMENTS 5,427,781 A 6/1995 DeFreitas et al.

OTHER PUBLICATIONS

Roßler et al., "No evidence of skin infection with *Chlamydia pneumoniae* in patients with cutaneous T cell Lymphoma." Clinical Microbiology and Infectious Diseases, CMI, vol. 9, No. 7, Jul. 2003, pp. 721-723.*
Abrams et al., "Sezary T-Cell activating factor is a *Chlamydia pneumoniae*-associated protein." Clinical and Diagnostic Laboratory Immunology, Nov. 1999, vol. 6, No. 6, pp. 895-905.*
Blasi et al., "*Chlamydia pneumoniae*." Clinical Pulmonary medicine, 2002, 9/1, pp. 6-12. Abstract Only.*
Langtry et al., "Azitromycin A review of its use in pediatric infectious diseases." Drugs, 1998, 56(2) pp. 273-297.*
Abrams et al., "Association between Sezary T Cell Activating Factor, *Chlamydia pneumoniae*, and cutaneous T cell lymphoma," Annals of the New York Academy of Sciences, vol. 941, Sep. 2001, pp. 69-85.*
Paulli and Berti, Haematologica, 2004, vol. 89, pp. 1372-1388.*
Tan R. S. -H et al., Mycosis fungoides—a disease of antigen persistence, British J. Dermatol., 1974; 91:607-616.
Gazdar A.F. et al., In Vitro Growth of Cutaneous T-Cell Lymphomas, Cancer Treatment Reports, 1979; 63:587-590.

Haynes B.F. et al., Cell Surface Differentiation Antigens of the Malignant T Cell in Sézary Syndrome and Mycosis Fungoides, J. Clin. Investig., 1981; 67:523-530.
Edelson R.L., Pathogenesis of T cell lymphoma of skin, Amer. Acad. Dermatol., 1983; 9:957-960.
Golstein M.M. et al., An OKT4+ T-Cell Population in Sézary Syndrome: Attempts to Elucidate Its Lack of Proliferative Capacity and Its Suppressive Effect, Scand. J. Immunol., 1986; 23:53-64.
Whittum-Hudson J.A. et al., Changes in conjunctival Lymphocyte populations induced by oral immunization with *Chlamydia trachomatis*, Current Eye Research, 1986; 5:973-979.
Sterry W. et al., CD4+ Cutaneous T-Cell Lymphomas Show the Phenotype of Helper/Inducer T Cells (CD45RA-, CDw29+), J. Invest. Dermatol., 1989; 93:413-415.
Abrams J.T. et al., A Clonal CD4-Positive T-Cell Line Established from the Blood of a Patient with Sezary Syndrome, J. Invest. Dermatol., 1991; 96:31-37.
Abrams J.T. et al., Malignant and Nonmalignant T Cell Lines From Human T Cell Lymphotropic Virus Type I-Negative Patients With Sézary Syndrome, J. Immunol., 1991; 146:1455-1462.
Hunt S.J. et al., Cutaneous T-cell lymphoma: Utility of lymphoma: Utility of antibodies to the variable regions of the human T-cell antigen receptor, J. Amer. Acad. Dermatol., 1992; 26:552-558.
Vowels B.R. et al., Extracorporeal Photochemotherapy Induces the Production of Tumor Necrosis Factor-α by Monocytes: Implications for the Treatment of Cutaneous T-Cell Lymphoma and Systemic Sclerosis, J. Investig. Dermatol., 1992; 98:686-692.
Grayston J.T. et al., *Chlamydia pneumoniae*, Strain Twar Pneumonia, Ann. Rev. Med., 1992; 43:317-23.
Leinonen M. et al., Pathogenetic mechanisms and epidemiology of *Chlamydia pneumoniae*, Eur. Heart J., 1993; 14 (Supplement K):57-61.
Gran J.T. et al., Pneumonia, Myocarditis and Reactive Arthritis due to *Chlamydia pneumoniae*, Scand. J. Rheumatol., 1993; 2:43-44.

(Continued)

*Primary Examiner*—Long V. Le
*Assistant Examiner*—Lisa V. Look
(74) *Attorney, Agent, or Firm*—Caesar, Rivise, Bernstein, Cohen & Pokotilow, Ltd.

(57) ABSTRACT

This invention provides methods of diagnosing and treating any C. pneumoniae infection of the skin including *C. pneumoniae*-associated diseases such as cutaneous T-cell lymphoma (CTCL), mycosis fungoides, Sézary syndrome, lymphomatoid papillosis, Ki-1 lymphoma, exfoliative exematous rash, and digitate parapsoriasis. This invention provides kits that are useful in the methods of the invention as well as for identifying new anti-chlamydial agents in treating skin infections. This invention includes a pharmaceutical vaccine composition comprising an antigen, including a full length antigenic determinant, such as any SAF positive determinant or portion thereof, which produces a detectable immune, humoral and/or cellular response to *C. pneumoniae*. The invention also includes a method of treating an active CTCL in a living being comprising delivering a therapeutically effective amount of a vaccine, wherein the vaccine comprises an agent, such as an inactivated *C. pneumoniae* material that produces a detectable immune, humoral and/or cellular response.

12 Claims, 27 Drawing Sheets

OTHER PUBLICATIONS

Beatty W.L. et al., Morphologic and antigenic characterization of interferon γ-mediated persistent *Chlamydia trachomatis* infection in vitro, Proc. Natl. Acad. Sci. USA, 1993; 90:3998-4002.

Abrams J.T. et al., Sézary T-Cell-activating Factor Induces Functional Interleukin 2 Receptors on T-Cells Derived from Patients with Sézary Syndrome, Cancer Res., 1993; 53:5501-5506.

Simon A.K. et al., Analysis of cytokine profiles in synovial T cell clones from chlamydial reactive arthritis patients: predominance of the Th1 subset, Clin. Exp. Immunol. 1993; 94:122-126.

Fivenson D.P. et al., Localization of clonal T cells to be epidermis in cutaneous T-cell lymphoma, J. Amer. Acad. Dermatol., 1994; 31:717-723.

Mielke V. et al., Clonal Disease In Early Cutaneous T-Cell Lymphoma, Dermatologic Clinics, 1994; 12:351-360.

Campbell L.C. et al., Detection of *Chlamydia pneumoniae* TWAR in Human Coronary Atherectomy Tissues, J. Infect. Dis., 1995; 172:585-588.

Hyman C.L. et al. Prevalence of Asymptomatic Nasopharyngeal Carriage of *Chlamydia pneumoniae* in Subjectively Healthy Adults: Assessment by Polymerase Chain Reaction-Enzyme Immunoassay and Culture, Clin. Infect. Dis., 1995; 20:1174-8.

Sarris A.H. et al., Cytokine Loops Involving Interferon-γ and IP-10, a Cytokine Chemotactic for CD4+ Lymphocytes: An Explanation for the Epidermotropism of Cutaneous T-Cell Lymphoma?, Blood, 1995; 86:651-658.

Koskiniemi M. et al., *Chlamydia pneumoniae* Associated with Central Nervous System Infections, Europ. Neurol., 1996; 36:160-163.

Koehler L. et al., Ultrastructural and molecular analyses of the persistence of *Chalymdia trachomatis* (serovar K) in human monocytes, Microbial Pathogenesis 1997; 22:133-142.

Jackow C.M. et al., Association of Erythrodermic Cutaneous T-Cell Lymphoma, Superantigen-Positive *Staphylococcus aureus*, and Oligoclonal T-Cell Receptor V B Gene Expansion, Blood, 1997; 89:32-40.

Balin B.J. et al., Identification and localization of *Chlamydia pneumoniae* in the Alzheimer's brain, Med. Microbiol. Immunol., 1998; 187:23-42.

J. Todd Abrams, Eric C. Vonderheid, Sonya Kolbe, Denah M. Appelt, E. James Arking, and Brian J. Balin. Sezary T-Cell Activating Factor is a *Chlamydia pneumoniae*-Associated Protein. Clinical and Diagnostic Laboratory Immunology, Nov. 1999, p. 895-905, vol. 6, No. 6.

J. Todd Abrams, Subrata K. Ghosh, and Elaine DeFreitas. Sezary T-Cell activating Factor Induces Functional Interleukin 2 Receptors on T-Cells Derived from Patients with Sezary Syndrome. Cancer Research 53, 5501-5506, Nov. 15, 1993).

Antimicrobial effects of phototherapy and photochemotherpay in vivo and in vitro. M Yoshimura, S.Namura, H. Akamatsu and T. Horio, British Journal of Dermatology 1996; 135:528-532.

Diabetic Foot Ulcers and *Chlamydia pneumoniae*: Innocent Bystander or Opportunistic Pathogen? (Reprinted) Arch Dermatol/ vol. 137, May 2001.

*Chlamydia pneumoniae* Associated with Central Nervous System Infections Eur Neurol 1996:36:160-163.

* cited by examiner

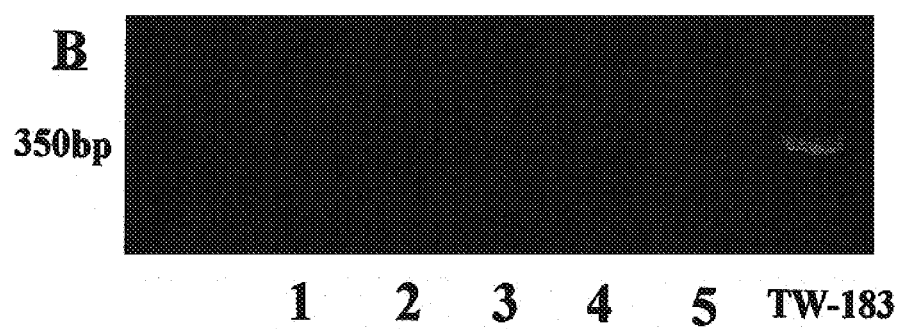

COMPOSITIONS, METHODS AND KITS FOR DIAGNOSIS AND TREATMENT OF *CHLAMYDIA PNEUMONIAE* INFECTIONS OF THE SKIN AND THOSE ASSOCIATED WITH CUTANEOUS T-CELL LYMPHOMA

RELATED APPLICATIONS

This application claims the benefit of the filing date of provisional application Ser. No. 60/242,907 filed on Oct. 24, 2000, the entire disclosure of which is incorporated by reference.

BACKGROUND OF THE INVENTION

The existence of a relationship between cutaneous T cell lymphoma (CTCL) and chronic stimulation of the immune system has been postulated for many years (Tan et al., 1974, British J. Dermatol. 91:607–616). A report by Duvic and co-workers (Jackow et al., 1997, Blood 89:32–40) has suggested an association between *Staphylococcus aureus* infection and CTCL. The report proposes that *S. aureus* provides chronic stimulation of the immune cells in CTCL patients, and that such stimulation may exacerbate the CTCL disease process. It is well established that a bacterial infection in the epidermis (i.e., skin) can lead to the production of inflammatory cytokines, resulting initially in lymphocytic infiltration and release of IFN-γ, followed by IL-10 production, and clonal expansion of epidermotropic T cells (Sarris et al., 1995, Blood 86:651–658). The Duvic report has added to the understanding of CTCL by providing a rational mechanism by which a bacterium could stimulate lymphocytic infiltration and promote chronic stimulation in CTCL patients.

The relationship between CTCL and *Chlamydia pneumoniae* infection has not been investigated. *C. pneumoniae* is an obligate intracellular pathogen that replicates within the cytoplasm of the cells in that it infects. *C. pneumoniae* was originally described as a respiratory pathogen (Leinonen, 1993, Eur. Heart J. 14: Supplement K, 57–61). However, the organism has been implicated in several non-pulmonary diseases such as meningoencephalitis, atherosclerosis and Alzheimer's disease (Campbell et al., 1995, J. Infect. Dis. 172:585–588; Gran et al., 1993, Scand. J. Rheumatol. 22:43–44; Koskiniemi et al., 1996, Eur. Neurol. 36:160–163; Balin et al., 1998, Med. Micro. & Immunol. 187:23–42). Epidemiological studies indicate that infection of adults by *C. pneumoniae* is common in all populations examined (Grayston, 1992, Annu. Rev. Med. 43:317–23; Hyman et al., 1995, Clin. Infect. Dis. 20:1174–1178; Leinonen, 1993, Eur. Heart J. 14: Supplement K, 57–61). Detection of significant anti-*C. pneumoniae* antibody titers rises with increasing age, with antibody levels peaking in the 6th–7th decades in most populations (Leinonen, 1993, Eur. Heart J. 14 (Supplement K):57–61).

Immunopathology is a general feature of *Chlamydia*-induced disease. Because *C. pneumoniae* is an intracellular pathogen, the immune system has difficulty clearing the infection. Thus, persistent Chlamydial infections are common and result in chronic inflammation caused by the presence of Th1/Th2 CD4+ T cells, as well as CD8+ cytotoxic/suppressor T cells, macrophages, and in some cases, B cells (Whittum-Hudson et al., 1986, Curr. Eye Res. 5:973–979). An example of the result of persistent Chlamydial infection is observed in the synovia of *C. trachomatis*-induced reactive arthritis (Simon et al., 1993, Clin. Exp. Immunol. 94:122–126). Interestingly, persistent Chlamydial infection may be maintained in part by Chlamydial induction of the expression of host proteins such as interferons (Beatty et al., 1989, Proc. Natl. Acad. Sci. USA 90:3998–4002; Simon et al., 1993, Clin. Exp. Immunol. 94:122–126). Thus, a balance appears to develop between host tissue survival and Chlamydial replication. It has been suggested that such a state of semi-latency can last for decades (Beatty et al., 1989, Proc. Natl. Acad. Sci. USA 90:3998–4002; Koehler et al., 1997, Microbial Pathogenesis 22:133–142).

As it has been shown that *C. pneumoniae* can travel to numerous areas of the body (Balin et al., 1998, Med. Micro. & Immunol. 187:23–42; Campbell et al., 1995, J. Infect. Dis. 172:585–588; Gran et al., 1993, Scand. J. Rheumatol. 22:43–44; Koskiniemi et al., 1996, Eur. Neurol. 36:160–163; Leinonen, 1993, Eur. Heart J. 14 (Supplement K):57–61), the inventors have focused on whether *C. pneumoniae* antigens could be detected in cells within the epidermis in patients with mycosis fungoides, the primary form of CTCL, or in the peripheral blood mononuclear cells of patients with Sézary Syndrome, the leukemic variant of CTCL. Leukemic CTCL represents a malignant clonal amplification of mature immune cells, including memory (CD45R0+), epidermotropic (CTLA+), helper T cells (CD4+), and CD3+ T cells (Edelson, 1983, J. Am. Acad. Dermatol. 9:957–960; Fivenson et al., 1994, J. Amer. Acad. Dermatol. 31:717–723; Haynes et al., 1981, J. Clinic. Investig. 67:523–530; Hunt et al., 1992, J. Am Acad. of Dermatol. 26:5552–5558; Mielke et al., 1994, Dermatol. Clinics. 12:351–360; Sterry and Mielke, 1989, J. Investig. Dermatol. 93:413–416). These cell types predominantly produce a Th2 cytokine profile (Vowels et al., 1992, J. Investig. Dermatol. 99:90–94).

Previous investigations have also focused on identifying the growth requirements for malignant cells in CTCL. A stimulatory factor has been identified that is capable of inducing proliferation of malignant Sézary cells. This factor has been named Sézary T cell Activatin Factor, or SAF (Abrams et al., 1993, Can. Res. 53:5501–5506; DeFreitas and Abrams, U.S. Pat. No. 5,427,781). SAF was originally described as being produced by the peripheral blood mononuclear cells of certain patients with Sézary Syndrome (Abrams et al., 1991, J. Immunol. 146:1455–1462), and was found to be a potent T cell mitogenic factor for malignant as well as non-malignant T cells (Abrams et al., 1993, Can. Res. 53:5501–5506; Abrams et al., 1991, J. Investig. Dermatol. 96:31–37; Abrams et al, 1991, J. Immunol. 146: 1455–1462). Accordingly, SAF has been used to establish cell lines from patients with Sézary Syndrome, some of which contained the predominant malignant clone (Abrams et al., 1991, J. Immunol. 146:1455–1462). SAF has enabled establishment of T cell lines from CTCL patients more readily than other methods (Gazdar et al., 1979, Cancer Treatment Rep. 63:587–590; Golstein et al., 1986, Scand. J. Immunol. 23:53–64). However, the role played by SAF in the development of CTCL remains to be elucidated.

CTCL represents a group of diseases for that distinct etiology is unknown and for which few effective treatments exist. In addition to understanding the mechanisms of CTCL pathology, there is a need to identify methods that are useful in identifying and treating CTCL. The present invention satisfies this need.

BRIEF SUMMARY OF THE INVENTION

The present invention provides a method of detecting *Chlamydia pneumoniae* infection in the skin of a mammal having a cutaneous T-cell lymphoma. The method comprises obtaining a sample from a mammal and performing an identification step in the sample for the presence or the absence of a *Chlamydia pneumoniae*-derived nucleic acid. The identification step further comprises performing one or more of a polymerase chain reaction and a reverse transcription-polymerase chain reaction.

In another aspect, the invention is a method of detecting *Chlamydia pneumoniae* infection in the skin of a mammal or a human having a cutaneous T-cell lymphoma. The method comprises obtaining a sample from the mammal and performing an identification step the presence or the absence of a *Chlamydia pneumoniae*-associated antigen wherein the presence of a *Chlamydia pneumoniae*-associated antigen in the sample constitutes the detection of a *Chlamydia pneumoniae* infection in the skin of a mammal having a cutaneous T-cell lymphoma. The identification step further comprises performing an analysis, wherein an antibody is contacted with the sample to determine the presence of a *Chlamydia pneumoniae*-associated antigen.

In another aspect, the invention is a method of treating a *Chlamydia pneumoniae* infection in a mammal or a human having a cutaneous T-cell lymphoma. The method comprises administering to said mammal or a human having a cutaneous T-cell lymphoma. The method comprises administering to said mammal one or more agents having anti-chlamydial activity in an amount sufficient to treat the *Chlamydia pneumoniae* infection of the mammal having said cutaneous T-cell lymphoma. The *Chlamydia pneumoniae* infection can be in the skin of said mammal. The agent having anti-chlamydial activity is selected from the group consisting of fluoroquinolone, a Macrolide™, tetracycline, a tetracycline derivative, penicillin, a penicillin derivative, and psoralen in combination with ultraviolet radiation (PUVA).

In another aspect, the invention is a method of treating an active cutaneous T-cell lymphoma in a mammal or a human having a *Chlamydia pneumoniae* infection. The method comprises administering to a mammal one or more agents having anti-chlamydial activity in an amount sufficient to inhibit or eradicate the *Chlamydia pneumoniae* infection, thereby treating said active cutaneous T-cell lymphoma in the mammal. The agent having anti-*chlamydia* activity is selected from the group consisting of fluoroquinolone, a macrolide, tetracycline, a tetracycline derivative, penicillin, a penicillin derivative, and psoralen in combination with ultraviolet radiation (PUVA). The active cutaneous T-cell lymphoma is selected from the group consisting of mycosis fungoides, Sézary syndrome, lymphomatoid papillosis, Ki-1 lymphoma, exfoliative exematous rash, and digitate parapsoriasis. The *Chlamydia pneumoniae* infection is selected from the group consisting of a skin infection, a blood infection, and a lymph node infection.

In another aspect, the invention is a method of treating *Chlamydia pneumoniae* infection in the skin of a mammal, where the mammal is a human. The method comprises administering to the mammal a combination of psoralen and ultraviolet radiation A (PUVA). A method of treating a *Chlamydia pneumoniae* infection can further include agents selected from a group of non-steroidal anti-inflammatory drugs (NSAIDS). PUVA can be used in combination with at least one agent selected from a group of non-steroidal anti-inflammatory drugs (NSAIDS).

In another aspect, the invention is a method of diagnosing an active cutaneous T-cell lymphoma in a mammal or in a human. The method comprises obtaining a sample from said mammal and identifying in the sample one or more of a *Chlamydia pneumoniae* nucleic acid, a *Chlamydia pneumoniae* protein and Sézary T-Cell activating factor. Such identification serves as an indication that the analyzed mammal is a mammal with an active cutaneous T-cell lymphoma. The *Chlamydia pneumoniae* protein can be selected from the group consisting of a lipopolysaccharide antigen and a major outer membrane protein.

In another aspect, the invention is a method of identifying a *Chlamydia pneumoniae* associated antigen.

In another aspect, the invention is a method of identifying anti-chlamydial agents. The method comprises obtaining keratinocytes from mammals, wherein the mammal is a human. In the method, the cultured keratinocytes are infected with *Chlamydia pneumoniae* and then cultured with various concentrations of at least on of anti-chlamydial agents (positive control) and agents with undefined anti-chlamydial activity.

In another aspect, the invention is a method of identifying the location of a chlamydial infection in a mammal, wherein said mammal is a human. In this method, a labeled agent capable of detecting a chlamydial infection is placed within the mammal; and the agent's presence is detected using standard imaging techniques. The agent can also be an anti-*Chlamydia pneumoniae*-associated antigen monoclonal antibody or any fragment or derivative thereof. The agent can also be a humanized anti-*Chlamydia pneumoniae*-associated antigen monoclonal antibody.

In another aspect, the invention is a method of preventing *Chlamydia pneumoniae* infection associated skin disorders comprising CTCL in a living being comprising delivering a vaccine. The vaccine comprises at least one agent selected from the group comprising inactivated *Chlamydia pneumoniae* materials that produce at least one of detectable immune, humoral and cellular response, and a therapeutically acceptable carrier. The vaccine can further comprise *Chlamydia pneumoniae* OMP, SAF, and other *Chlamydia pneumoniae* proteins further comprising HSP-60 and type III secretion system proteins (YOP), DNA isolated from *Chlamydia pneumoniae*.

In another aspect, the invention is a kit for detecting the presence of a *C. pneumoniae* protein, obtained from the skin of a living being, comprised of at least one antibody to the *Chlamydia pneumoniae* protein or a portion thereof either bound to a solid support or labeled with an agent to detect the presence of *Chlamydia pneumoniae*. The antibodies comprise those reacting with chlamydial-associated outer membrane proteins, SAF, and LPS. Kits for detecting the presence of a *C. pneumoniae* nucleic acids from skin of a living being or cell culture, further comprise a detectably labeled nucleic acid probe or a PCR primer.

In another aspect, the invention is a pharmaceutical vaccine composition comprising at least one anti-chlamydial agent comprising a full length antigenic determinant, a SAF-positive determinant, or any portion thereof, wherein said agent produces a detectable immune response, humoral and/or cellular to *Chlamydia*; and a therapeutically acceptable carrier.

In another aspect, the invention is a pharmaceutical at least one agent selected from the group of inactivated *Chlamydia pneumoniae* materials that produce at least one of detectable immune, humoral and cellular response and a therapeutically acceptable carrier.

In another aspect, the invention is a method of treating an active cutaneous T-cell lymphoma in a living being comprising delivering a therapeutically effective amount of a vaccine. The vaccine comprises at least one agent selected from the group of *Chlamydia pneumoniae* materials that produce at least one detectable immune, humoral and cellular response, said materials being inactivated and a therapeutically acceptable carrier.

BRIEF DESCRIPTION OF THE DRAWINGS

FIG. 5B is an image of a gel depicting a reverse transcriptase-polymerase chain reaction (RT-PCR) analysis specific for *C. pneumoniae* using DNA obtained from patients with CTCL. A nested primer set specific for the omp-A gene of *C. pneumoniae* (i.e., omp-A primer sequence ID 1–4, see Methods) was used. The image depicts the amplification products obtained using RNA extracted from the lymph nodes of patients with tumor stage mycosis fungoides (lanes 1, 2), or with Sézary syndrome (lanes 3–5). Briefly, the RNA was treated with DNase and exposed to MuLV reverse transcriptase. Three microliters from each sample were subjected to PCR using the same omp-A specific primers as used for the DNA PCR analysis depicted in FIG. 5A. Positive control DNA obtained from *C. pneumoniae* TW-183 bacteria exhibited a band at about 350 bp as well as two bands having higher molecular masses. No amplification produces were detected in the "no RT" control, i.e., water only without primers.

DETAILED DESCRIPTION OF THE INVENTION

Figure 1A:
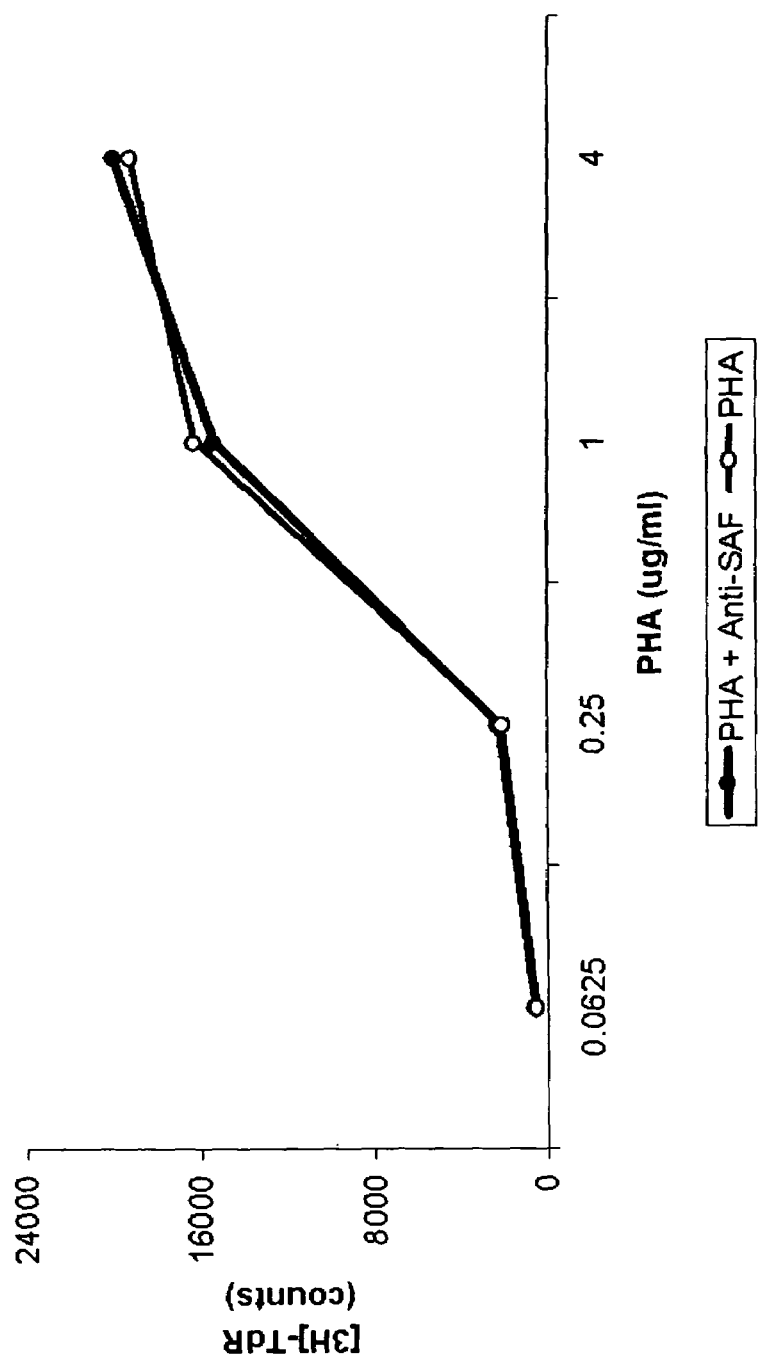
FIG. 1A is a graph depicting the inhibition of SAF bioactivity by anti-SAF. Twenty-five micrograms per milliliter of anti-SAF was cultured with peripheral blood mononuclear cells (PBMC) from a healthy donor along with various amounts of phytohaemagglutinin (PHA) in the presence of 15 units per milliliter of rIL-2 for 72 hours. Cells were pulsed with tritiated thymidine for the final 6 hours, harvested, and prepared for liquid scintillation counting. Data represent the means of triplicate cultures. The standard error for each data set was less than 10% of the mean.
Figure 1B:
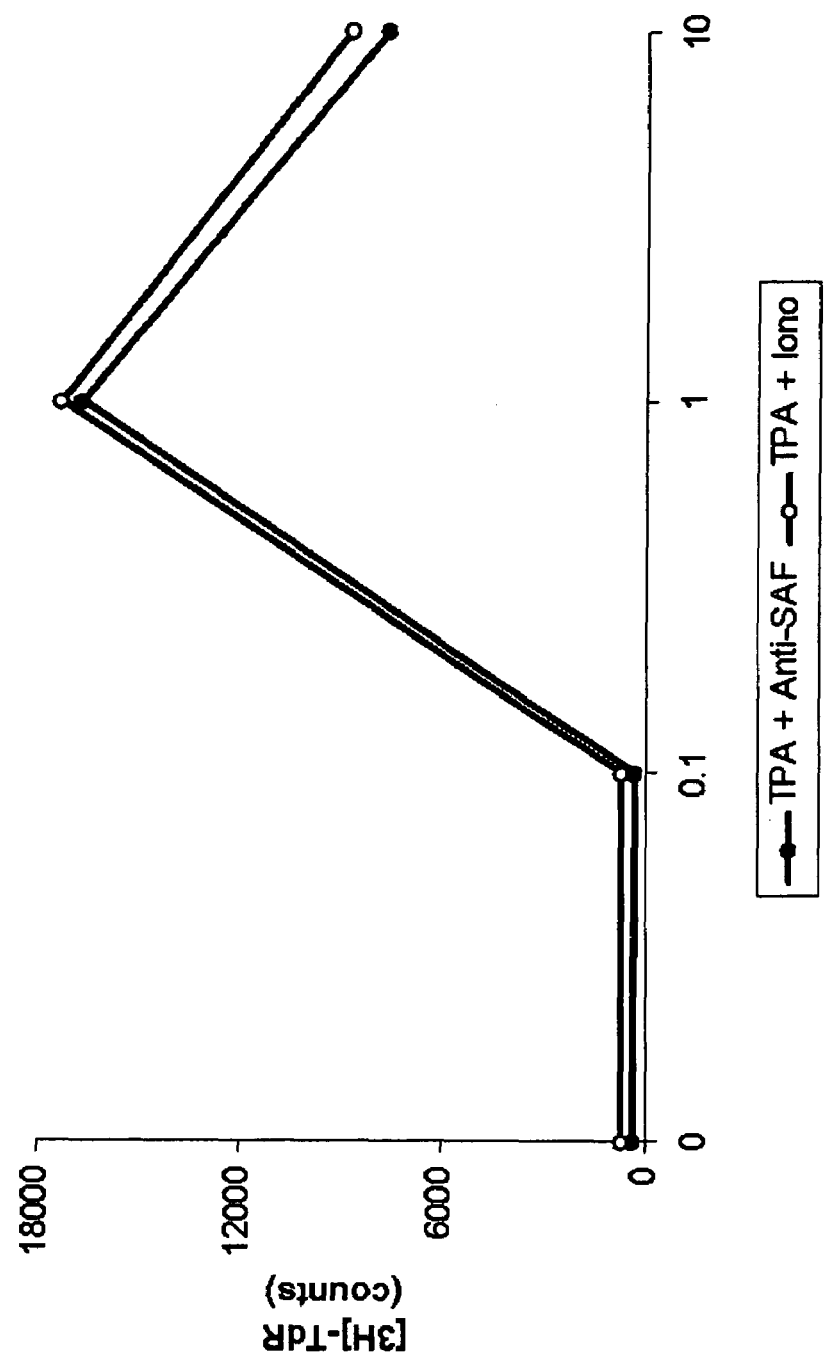
FIG. 1B is a graph depicting the inhibition of SAF bioactivity by anti-SAF. Twenty five micrograms per milliliter of anti-SAF was cultured with PBMC from a healthy donor along with various amounts of a tetradecanoylphorbol acetate (TPA) and Ionomycin in the presence of 15 units per milliliter of rIL-2 for 72 hours. Cells were pulsed with tritiated thymidine for the final 6 hours, harvested, and prepared for liquid scintillation counting. Data represent the means of triplicate cultures. The standard error for each data set was less than 10% of the mean.
Figure 1C:
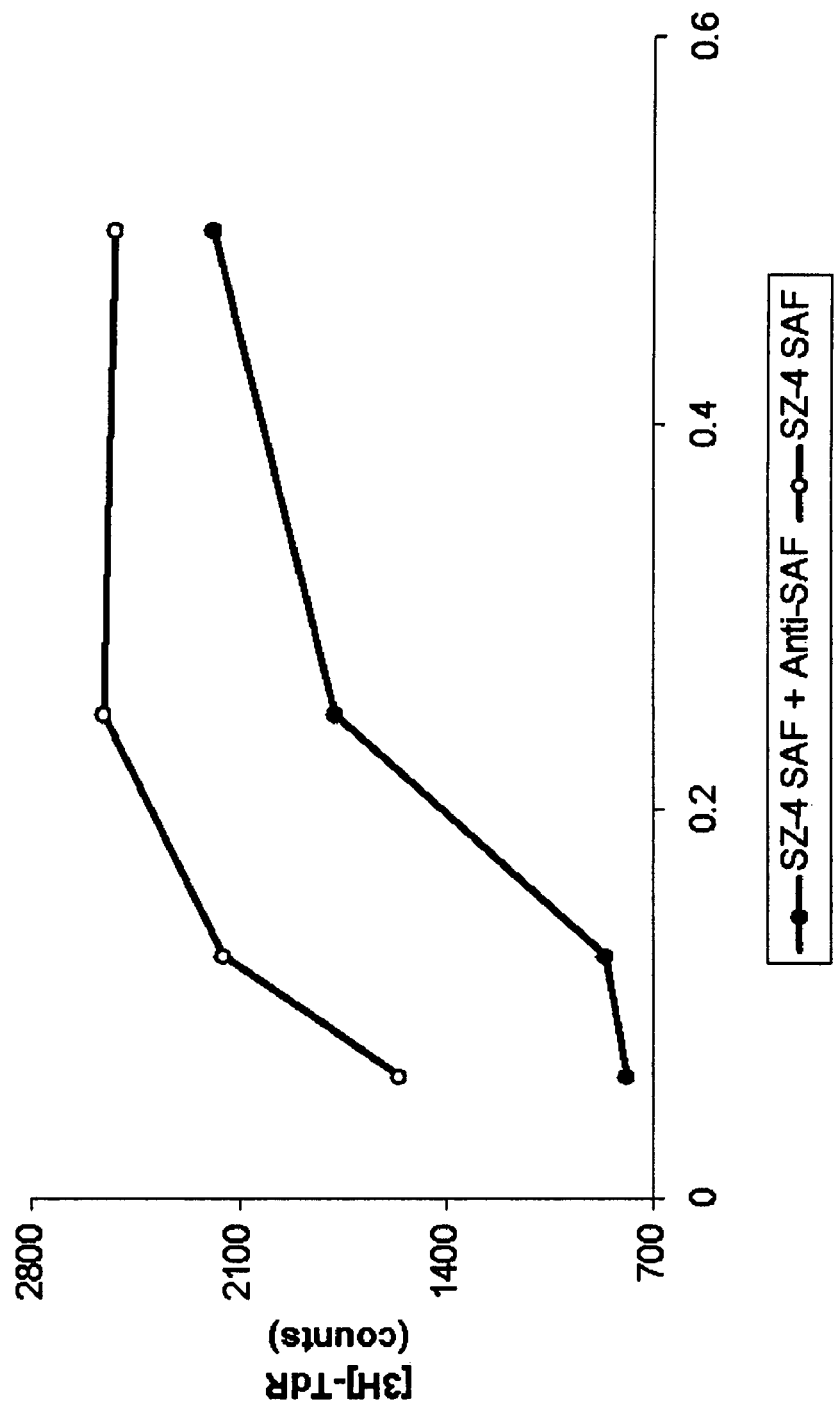
FIG. 1C is a graph depicting the inhibition of SAF bioactivity by anti-SAF. Twenty five micrograms per milliliter of anti-SAF was cultured with PBMC from a healthy donor along with various amounts of cell line-derived (SZ-4-SAF) SAF in the presence of 15 units per milliliter of rIL-2 for 72 hours. Cells were pulsed with tritiated thymidine for the final 6 hours, harvested, and prepared for liquid scintillation counting. Data represent the means of triplicate cultures. The standard error for each data set was less than 10% of the mean.
Figure 1D:
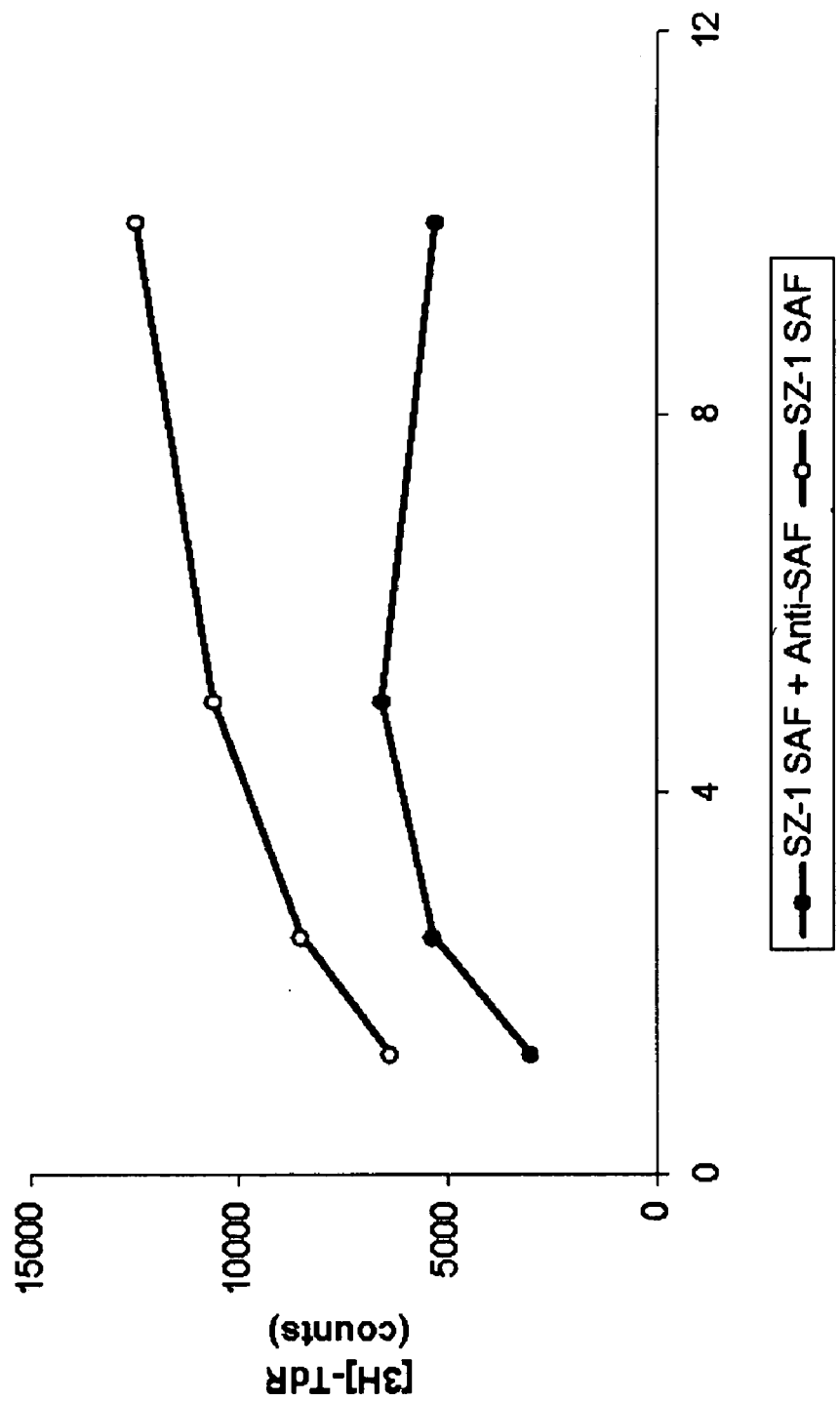
FIG. 1D is a graph depicting the inhibition of SAF bioactivity by anti-SAF. Twenty five micrograms per milliliter of anti-SAF was cultured with PBMC from a healthy donor along with various amounts of PBMC-derived SAF (SZ-1 SAF) in the presence of 15 units per milliliter of rIL-2 for 72 hours. Cells were pulsed with tritiated thymidine for the final 6 hours, harvested, and prepared for liquid scintillation counting. Data represent the means of triplicate cultures. The standard error for each data set was less than 10% of the mean.

The present invention includes methods of detecting and treating a *Chlamydia pneumoniae* infection in the skin of a mammal, preferably, a human. The invention additionally provides methods of diagnosing and treating a cutaneous T-cell lymphoma, such as mycosis fungoides or Sézary syndrome, in a mammal, such as a human. The invention further provides kits that are useful in identifying new agents for treatment of Chlamydial infection in the skin and provides kits that are useful for other method s described herein.

Definitions

As used herein, each of the following terms has the meaning associated with it in this section.

The articles "a" and "an" are used herein to refer to one or to more than one (i.e. to at least one) of the grammatical objects of the article. By way of example, "an element" means one element or more than one element.

As used herein, an "agent having anti-chlamydial activity" means a composition of matter that, when delivered to a cell, is capable of one or more of preventing the growth or propagation of a *C. pneumoniae* bacterium in the cell, preventing infection of the cell by a *C. pneumoniae* bacterium, preventing expression in the cell of *C. pneumoniae*-associated nucleic acids or proteins, and reversing a physiological effect of infection of the cell by *C. pneumoniae* bacterium.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

An "isolated nucleic acid", as used herein, refers to a nucleic acid sequence, segment, or fragment that has been purified from the sequences that flank it in a naturally occurring state, e.g., a DNA fragment that has been removed from the sequences that are normally adjacent to the fragment e.g., the sequences adjacent to the fragment in a genome in that it naturally occurs. The term also applies to nucleic acids that have been substantially purified from other components that naturally accompany nucleic acid, e.g., RNA or DNA or proteins that naturally accompany it in the cell.

As used herein, the term "*Chlamydia pneumoniae* nucleic acid" refers to a molecule comprising a deoxyribonucleic acid or a ribonucleic acid, e.g., RNA or DNA or proteins that naturally accompany it in the cell, that can be isolated, amplified, or otherwise derived from a *C. pneumoniae* bacterium. A *C. pneumoniae* nucleic acid can include a nucleic acid that is either complementary to or homologous with a *C. pneumoniae* nucleic acid.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of that is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Complementary" as used herein, refers to the subunit sequence complementarily between two nucleic acid molecules, e.g., two DNA molecules or two RNA molecules. When a subunit position in both of the two molecules is occupied by a complementary monomeric subunit, e.g., if one position in each of two DNA molecules is occupied by adenine and the other is occupied by a thymidine, then they are complementary at that position. Similarly, if one position in each of two DNA molecules is occupied by guanine and the other is occupied by a cytosine, then they too are complementary at that position. The degree of complementarity between two sequences is a direct function of the number of positions occupied by complementary bases, e.g., if half (e.g., five positions in a polymer ten subunits in length) of the positions in two compound sequences contain complementary bases then the two sequences share 50% complementarity, if 90% of the positions, e.g., 9 of 10, contain bases complementary to each other, the two sequences share 90% complementarity. By way of example, the DNA sequences 5'ATTGCC3' and 3'GGCCGG5' share 50% complementarity.

"Homologous" as used herein, refers to the subunit sequence similarity between two polymeric molecules, e.g., between two nucleic acid molecules, e.g., two DNA molecules or two RNA molecules, or between two peptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3' ATTGCC 5' and 3' TATGCG 5' share 50% homology. Any of a variety of known algorithms may be used to calculate the percent homology between two nucleic acids or two proteins of interest and these are well-known in the art.

As used herein, a "*Chlamydia pneumoniae* protein" refers to a protein that is encoded by a gene or a portion of a gene that is either identified within the genome of *C. pneumoniae* or derived from the genome of *C. pneumoniae*. This term is used herein to include a protein that is substantially homologous with a *C. pneumoniae* protein.

As used herein, the term "*Chlamydia pneumoniae*-associated antigen" refers to an antigenic molecule that can be demonstrated to be associated with one or more of the presence of *C. pneumoniae* bacteria, proteins, or nucleic acids, the expression of a *C. pneumoniae* protein, and the expression of a *Chlamydia pneumoniae* nucleic acid. The present disclosure relates the Sézary T cell Activating Factor, SAF, as an exemplary *C. pneumoniae*-associated antigen that is also associated with CTCL. The invention should not be construed as being limited solely to this example, as other disease-associated molecules that are currently unknown, may be associated with *C. pneumoniae*, and may be identified using the methods of the invention. Once known, such molecules may additionally be useful in the methods of the invention.

A disorder is "treated" if one or more of the frequency, the severity, and the duration of either the disorder or a symptom of the disorder are reduced. By way of example, a CTCL is treated if the severity of epithelial symptoms associated with the disease is reduced.

The present disclosure describes CTCL and *C. pneumoniae* infections as exemplary disorders that may be treated according to the methods of the invention. The invention should not be construed as being limited solely to these examples, as other leukocyte- or keratinocyte-associated diseases that are currently unknown, once known, may also be treatable using the methods of the invention.

As used herein, the term "identifying agent" means a composition of matter that, when delivered to a cell, facilitates detection of the cell. Numerous identifying agents are known and described in the literature. By way of example, enzymes, such as β-galactosidase, that are capable of catalyzing a reaction involving a chromogenic substrate may be used. Further by way of example, compounds, the presence of which may be directly detected may be used, such as compounds that emit gamma radiation or fluoresce, which may be detected using an appropriate detection apparatus.

As used herein, an "instructional material" includes a publication, a recording, a diagram, or any other medium of expression that can be used to communicate the usefulness of an anti-chlamydial composition, and that describes outlines, or diagrams a method described herein. The instructional material of the kit included in the present invention may, for example, be affixed to a container that comprises an anti-chlamydial composition, or be shipped together with a container that comprises the anti-chlamydial composition. Alternatively, the instructional material may be shipped separately from the container with the intention that the instructional material and the anti-chlamydial composition be used cooperatively by the recipient.

The term "pharmaceutically acceptable carrier" means a chemical composition with which a pharmaceutically active agent can be combined and that, following the combination, can be used to administer that agent to a subject (e.g. a mammal such as a human).

The term "physiologically acceptable" ester or salt means an ester or salt form of a pharmaceutically active agent that is compatible with any other ingredients of the pharmaceutical composition and that is not deleterious to the subject to whom the composition is to be administered.

Description

The present invention stems from the discovery that a protein referred to as Sézary T cell Activating Factor (SAF) is a *Chlamydia pneumoniae*-associated protein. While it is known that SAF stimulates the malignant Sézary T cells involved in the pathogenesis of Sézary syndrome, a type of cutaneous T cell lymphoma (CTCL), until the present discovery, it was not known that SAF is a *C. pneumoniae*-associated protein. It has further been discovered herein, that SAF is present in the skin of patients with mycosis fungoides, the predominant form of cutaneous T cell lymphoma, that SAF is associated with *C. pneumoniae* bacteria in the skin, and that SAF is associated with active CTCL disease states.

Accordingly, the present invention includes diagnostic methods, such as a method of detecting a *C. pneumoniae* infection in a mammal and a method of diagnosing an active cutaneous T-cell lymphoma in a mammal, therapeutic methods, such as a method of treating a *C. pneumoniae* infection in a mammal and a method of treating an active cutaneous T-cell lymphoma in a mammal, and analytical methods, such as a method of identifying a *C. pneumoniae*-associated antigen in a mammal.

Methods

A *C. pneumoniae* infection that is either identified or treated by a method described herein can be located, for example, substantially in the skin (i.e. cutaneous tissue) of a mammal, preferably, a human.

The methods described herein require at least one analysis to be performed on a sample either from a mammal or from a population of cultured cells. A sample from a mammal, that is useful in the methods described herein, includes substantially any type of biological sample obtained from the mammal, preferably, a skin sample, a blood sample, and a lymph node sample. The term "biological sample" is further intended to include tissues, cells and biological fluids isolated or otherwise derived from a mammal, as well as tissues, cells and fluids present within a mammal. That is, the diagnostic, therapeutic, and analytical methods described herein can be used to detect mRNA, protein, or genomic DNA in a biological sample in vitro as well as in vivo. By way of example, a useful biological sample can contain one or more of protein molecules, mRNA molecules, and genomic DNA molecules obtained either from a mammal or from mammalian cells in culture. A preferred biological sample comprises whole cells isolated by conventional means either from a mammal or from mammalian cells in culture.

Several methods described herein include detecting the presence or absence of a *C. pneumoniae* protein, *C. pneumoniae*-associated antigen, or *C. pneumoniae* nucleic acid in a biological sample obtained from the mammal. These methods can comprise obtaining a biological sample from mammal and contacting the biological sample with a compound or an agent capable of detecting a *C. pneumoniae* protein, *C. pneumoniae*-associated antigen, or *C. pneumoniae* nucleic acid (e.g., mRNA, genomic DNA) such that the presence of a *C. pneumoniae* protein, *C. pneumoniae*-associated antigen, or *C. pneumoniae* nucleic acid is detected in the biological sample.

In other embodiments, the methods can further comprise obtaining a control biological sample from a control mammal or from a population of cultured cells that do not have either a *C. pneumoniae* infection or a *C. pneumoniae*-associated disorder, such as a CTCL. In these methods, the control sample is contacted with a compound or agent capable of detecting a *C. pneumoniae* protein, *C. pneumoniae*-associated antigen, or *C. pneumoniae* nucleic acid, such that the presence, or lack thereof, of the *C. pneumoniae* protein, *C. pneumoniae*-associated antigen, or *C. pneumoniae* nucleic acid is detected in the biological sample. Also in these methods, the level of a *C. pneumoniae* protein, a *C.*

*pneumoniae*-associated antigen, or a *C. pneumoniae* nucleic acid in the control sample is compared with the level of the same *C. pneumoniae* protein, *C. pneumoniae*-associated antigen, or *C. pneumoniae* nucleic acid in the sample from the mammal to be tested.

Methods described herein that require the detection of nucleic acids in either a sample obtained from a mammal (e.g., a human patient sample) or cultured cells, can include, for example, the steps of obtaining a sample comprising cells from a mammal, isolating a nucleic acid (e.g., DNA, RNA, or both) from the cells of the sample, and contacting the nucleic acid sample with one or more primers that specifically hybridize to a *C. pneumoniae* nucleic acid or a gene encoding a *Chlamydia pneumoniae*-associated antigen, under conditions such that hybridization and amplification of the gene (if present) occurs. These methods also comprise either detecting the presence or absence of an amplification product, or detecting the size of the amplification product and comparing the size of the amplification product to the size of the amplification product obtained with a control sample.

Methods for detecting nucleic acids using a PCR or an RT-PCR are well known in the art and are provided in standard references (e.g., Innis et al., ed., 1990, In: PCR Protocols, Academic Press, Inc., San Diego). PCR or RT-PCR may be used as a preliminary amplification step in conjunction with any other well-known techniques used for detecting nucleic acids in a sample that are described herein.

Alternative nucleic acid amplification-detection procedures that may be useful in the methods of the invention include, but are not limited to: self-sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers. Other well-known techniques for the detection of nucleic acids, such as Northern hybridizations, in situ hybridizations, and Southern hybridizations, can also be used in the methods of the invention.

A preferred agent for detecting mRNA or genomic DNA comprising a portion of a *C. pneumoniae* gene sequence or a *C. pneumoniae*-associated antigen gene sequence is a labeled nucleic acid probe capable of hybridizing to mRNA or genomic DNA comprising a portion of a *C. pneumoniae* gene sequence or a *C. pneumoniae*-associated antigen gene sequence. The nucleic acid probe can be complementary to or homologous with a portion of a *C. pneumoniae* gene sequence or a gene sequence encoding a *Chlamydia pneumoniae*-associated antigen, and comprising a nucleotide sequence of at least 15, 30, 50, 100, 250 or 500 contiguous nucleotides that is sufficient to specifically hybridize under stringent conditions to a mRNA or DNA encoding a *C. pneumoniae* protein or a *Chlamydia pneumoniae*-associated antigen. Preferred probes would be specific for but not limited to MOMP and 16s rRNA genes that will comprise the nucleotide sequences for detection of the presence of *C. pneumoniae* bacteria.

Methods described herein that include the detection of either a *C. pneumoniae* protein, such as the major outer membrane protein (MOMP) or the *C. pneumoniae* lipopolysaccharide (LPS), or a *C. pneumoniae*-associated antigen, such as SAF, can include substantially any compatible protein detection methods known in the art. Examples of useful protein detection methods include, but are not limited to, in vitro techniques, such as enzyme linked immunosorbent assays (ELISAs), Western blots, immunoprecipitations and immunofluorescence, and, in vivo techniques, such as introducing into a subject a labeled antibody directed against either a *C. pneumoniae* protein or a *C. pneumoniae*-associated antigen. For example, the antibody can be labeled with a radioactive marker whose presence and location in a subject can be detected by standard imaging techniques.

A preferred agent for detecting either a *C. pneumoniae* protein or a *C. pneumoniae*-associated antigen is an antibody capable of binding to either a *C. pneumoniae* protein or a *C. pneumoniae*-associated antigen, preferably an antibody with a detectable label. Antibodies can be polyclonal, or more preferably, monoclonal. Preferable antibodies would be reactive with either *C. pneumoniae* heat shock protein 60, *C. pneumoniae* major outer membrane proteins, SAF, *C. pneumoniae* lipopolysaccharide, or to *Chlamydia* type three secretion molecules (YOP). An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Analytical Methods

The invention further includes a method of identifying a *C. pneumoniae*-associated antigen. This method comprises obtaining a sample from a mammal and contacting the sample with one or more of an isolated nucleic acid having a nucleotide sequence that is homologous with or complementary to a nucleotide sequence derived from *C. pneumoniae*; an isolated nucleic acid having a nucleotide sequence that is homologous with or complementary to the nucleotide sequence encoding a suspected antigen; and an identifying agent that specifically binds to, adsorbs onto, or chemically reacts with one or more of an isolated nucleic acid that is homologous with or complementary to either of *C. pneumoniae* and the suspected antigen, and an amino acid sequence of either of *C. pneumoniae* and the suspected antigen. This method is illustrated herein in the Examples, and further comprises analyzing the sample to determine the presence or absence of a nucleic acid or amino acid sequence associated with *C. pneumoniae* and the presence or absence of a nucleic acid or amino acid sequence associated with the suspected antigen. Preferred nucleotide primers include but are not limited to those that amplify *C. pneumoniae* gene sequences as listed in Table 1. In addition, the method comprises determining the extent to that the presence of *C. pneumoniae* is associated with the presence of the suspected antigen; whereby determining a significant association between the presence of *C. pneumoniae* and the presence of the suspected antigen is an indication that the suspected antigen is a *C. pneumoniae* associated antigen.

TABLE 1

Chlamydia pneumoniae specific primers

| Gene | Primer used | Sequence | Seq. ID No |
|---|---|---|---|
| MOMP | External plus strand | 281-CTGCAAACTATACTACTGCC-300 | #1 |
| MOMP | External minus strand | 1073-CCTACAGTAACTCCACAAGCT-1053 | #2 |
| MOMP | Internal plus strand | 390-TCGCTTTGATGTTTTCTGTACT-411 | #3 |
| MOMP | Internal minus strand | 730-AAGCAACGCCTTTATAGCCC-711 | #4 |
| 16s rRNA | External plus strand | 71-ATAATGACTTCGGTTGTTAT-90 | #5 |
| 16s rRNA | External minus strand | 1465-TATAAATAGGTTGAGTCAAC-1446 | #6 |
| 16s rRNA | Internal plus strand | 243-TATGCGATATCAGCTTGTTGGTGG-266 | #7 |
| 16s rRNA | Internal minus strand | 976-GCATCGAATTAAACCACATGCTCC-953 | #8 |
| MOMP | External plus strand | 26-TATTATCCGCCGCATTTG-43 | #9 |
| MOMP | External minus strand | 567-AGAGAAAGAGGTGTCTGTGT-548 | #10 |
| MOMP | Internal plus strand | 115-ACAATATGGGAGGGTGCTGCA-135 | #11 |
| MOMP | Internal minus strand | 462-GAGATTGAACGCTGTAGAG-444 | #12 |

The method of identifying a *C. pneumoniae* associated antigen can alternatively comprise obtaining a sample from a mammal and contacting the sample with one or more of an antibody specific for a *C. pneumoniae* protein, such as SAF, or an antibody specific for the suspected antigen that is not a *C. pneumoniae* protein, and an identifying agent that is capable of specifically binding to, adsorbing onto, or chemically reacting with an amino acid sequence of either a *C. pneumoniae* protein or the suspected antigen. This alternative method is illustrated herein in the Example, and can further comprise analyzing the sample to determine the presence of an amino acid sequence associated with either a *C. pneumoniae* or a suspected antigen, and determining the extent to which the presence of *C. pneumoniae* coincides with the presence of the suspected antigen. According to this method, determining a significant coincidence between the presence of *C. pneumoniae* and the presence of the suspected antigen is an indication that the suspected antigen is a *C. pneumoniae*-associated antigen.

One skilled in the art will understand that a *C. pneumoniae*-associated antigen identified as described above that is associated with or that becomes associated with a disorder, may be useful in the diagnostic methods, treatment methods, and reagent screening methods described herein. By way of example, a *C. pneumoniae*-associated antigen identified as above, that is found to be associated with or involved in the pathology of a skin disease in a mammal, may be used according to a method described herein to diagnose the associated skin disease in the mammal, and the methods described herein for treating a *C. pneumoniae* infection in a mammal may further be useful in treating the associated skin disease in the mammal.

Diagnostic Methods

The present invention includes a method of detecting *C. pneumoniae* infection in the skin of a mammal such as in a mammal having a cutaneous T-cell lymphoma. This method can include subjecting a sample from the mammal to one or more of a PCR and an RT-PCR. The amplification of a *C. pneumoniae* nucleic acid (e.g. RNA or DNA) in a PCR or RT-PCR comprising the sample from the mammal constitutes the detection of *C. pneumoniae* infection in the mammal.

Alternatively, the preceding method can comprise contacting the sample from the mammal with an antibody that is specific for either a *C. pneumoniae* protein or a *C. pneumoniae*-associated antigen, such as SAF. According to this method, the presence of either a *C. pneumoniae* or a *C. pneumoniae*-associated antigen in the sample, is an indication that a *C. pneumoniae* bacterium is present in the sample, and thus, constitutes the detection of *C. pneumoniae* infection in the mammal.

One skilled in the art would appreciate, based upon the disclosure herein, that the presence a *C. pneumoniae* protein or a *C. pneumoniae*-associated antigen can be assessed in keratinocytes. Thus, the skilled artisan would appreciate that the invention encompasses detection of these proteins and/or antigens in regions of the skin, including but not limited to, stratum spinosum, the stratum granulosum, the stratum germinativum, as well as in histiocytes, and Langerhans dendritic cells, and the like.

According to the above methods, either the identification of a *C. pneumoniae* nucleic acid in a sample from the mammal or the determination that either a *C. pneumoniae* protein or a *C. pneumoniae*-associated antigen is present in the sample constitutes the detection of a *C. pneumoniae* infection in the skin of a mammal. In this application, the sample that is obtained from the mammal for analysis is a skin (i.e. cutaneous tissue) sample.

In another aspect, the invention includes a method of diagnosing an active cutaneous T-cell lymphoma, such as mycosis fungoides or Sézary syndrome, in a mammal. This method comprises obtaining a sample from the mammal and identifying in the sample one or more of a *C. pneumoniae* nucleic acid, a *C. pneumoniae* protein, and SAF. According to this method, an identification in the sample of a *C. pneumoniae* nucleic acid, a *C. pneumoniae* protein, or SAF is an indication that the mammal has an active cutaneous T-cell lymphoma. By way of example, this method encompasses diagnosing an active CTCL in a human by identifying in a skin sample from the human a *C. pneumoniae* nucleic acid using PCR or RT-PCR, or identifying in the skin sample either a *C. pneumoniae* protein, such as a lipopolysaccharide antigen or a major outer membrane protein, or a *C. pneumoniae*-associated antigen, such as SAF, using an ELISA.

Therapeutic Methods

Encompassed by the present invention is a method of treating a *C. pneumoniae* infection in a mammal having a cutaneous T-cell lymphoma. This method comprises administering to a mammal one or more agents having anti-chlamydial activity in an amount sufficient to treat the *C. pneumoniae* infection. Preferably, the infection is located substantially in the skin of the mammal.

The invention additionally includes a method of treating an active cutaneous T-cell lymphoma (CTCL) in a mammal having a *C. pneumoniae* infection. In this method, one or more agents having anti-chlamydial activity are administered to the mammal in an amount sufficient to inhibit the *C. pneumoniae* infection, and thereby treat the active CTCL in the mammal.

For the treatment methods described herein, a CTCL can include, without limitation, mycosis fungoides, Sézary syndrome, lymphomatoid papillosis, Ki-1 lymphoma, exfoliative exematous rash, and digitate parapsoriasis, and the like.

The skilled artisan would appreciate, based upon the disclosure provided herein, that the treatment methods described herein could be applied to treating disorders in addition to CTCL that are associated with *C. pneumoniae* infection in the skin.

In further regard to the treatment methods of the invention, an agent having anti-chlamydial activity can be any agent that is known or becomes known, that is useful in the methods of the invention. Examples of anti-chlamydial agents that can be used in the methods of the invention include, but are not limited to, fluoroquinolone, macrolides, tetracycline derivatives, and/or the elimination of the active forms of *Chlamydia* using penicillins and derivatives thereof, as well as psoralen in combination with ultraviolet radiation (PUVA).

The skilled artisan would appreciate, based upon the disclosure provided herein, that the anti-chlamydial agent encompasses a vaccine. That is, a "vaccine," as the term is used herein, means any antigen, including but not limited to, a full length antigenic determinant, including any SAF positive determinant, or any portion thereof, that produces a detectable immune response, humoral and/or cellular, to *Chlamydia* when administered to a mammal, preferably a human, compared with the immune response in an otherwise identical mammal to that said antigenic determinant is not administered.

The skilled artisan would be able, armed with the teachings of this invention, to readily prepare such vaccines comprising whole or fractionated determinants. Further, useful fractionated determinants that are SAF positive can be readily identified and isolated using the methods disclosed herein or those well-known in the art. For example such a vaccine could be produced by preparing purified bacterial bodies from infected cells cultured through centrifugation, followed by ultraviolet inactivation, and followed by heating to a boil. The preparation would then be sonicated until completely dispersed, after which specific proteins, such as SAF positive determinants, may be purified. Preparations of whole or purified bacterial lysate would be injected in physiologic solution in the presence or absence of rIL-12. Injections would be repeated until a titer of greater than 1:512 is obtained to be considered immunized.

An anti-chlamydial agent (also referred to herein as an "active compound") of the invention can be incorporated into a pharmaceutical composition suitable for administration. Such compositions typically comprise the anti-chlamydial agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated.

It is understood that appropriate doses of anti-chlamydial agents depend upon a number of factors within the ken of the ordinarily skilled physician, veterinarian, or researcher. The dose(s) of these agents will vary, for example, depending upon the identity, size, and condition of the subject (i.e., mammal) or sample being treated, further depending upon the route by that the composition is to be administered, if applicable, and the effect that the practitioner desires the agent to have upon the nucleic acid or polypeptide of the invention. Exemplary doses of an anti-chlamydial agent include milligram or microgram amounts per kilogram of subject or sample weight (e.g. about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of one of the anti-chlamydial agents depends upon the potency of the agent with respect to the infection to be treated. When one or more of these agents is to be administered to a mammal (e.g. a human) in order to treat an infection according to a method of the invention, a physician, veterinarian, or researcher can, for example, prescribe a relatively low dose at first, subsequently increasing the dose until an appropriate response is obtained. In addition, it is understood that the specific dose level for any particular mammalian subject will depend upon a variety of factors including the activity of the specific agent employed, the age, body weight, general health, gender, and diet of the subject, the time of administration, the route of administration, the rate of excretion, any drug combination, and the degree of the infection to be treated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

In view of the number of well-characterized anti-chlamydial agents, the determination of pharmaceutical parameters that are necessary to perform the treatment methods of the invention, such as sufficiently bactericidal dosages and appropriate routes of administration, are considered to be well within the ability of a skilled artisan such as a physician, veterinarian, or researcher.

Kits

The invention encompasses kits for detecting the presence of a *C. pneumoniae* protein, a *C. pneumoniae*-associated antigen, or a *C. pneumoniae* nucleic acid in a biological sample (i.e., a test sample) that is either obtained from a mammal or from cells in culture. The kits described herein can be used to determine if a mammal is infected with *C. pneumoniae* or if a mammal is suffering from a form of CTCL, such as mycosis fungoides or Sézary syndrome. Alternatively, the kits of the invention can be used to treat a *C. pneumoniae* infection or a CTCL. For example, the kit can comprise a labeled compound or identifying agent capable of detecting a *C. pneumoniae* protein, a *C. pneumoniae*-associated antigen, or a *C. pneumoniae* nucleic acid in a biological sample and means for determining the amount of the *C. pneumoniae* protein, *C. pneumoniae*-associated antigen, or *C. pneumoniae*-associated antigen, or a nucleic acid probe that binds to a nucleic acid encoding a *C. pneumoniae* protein or a *C. pneumoniae*-associated antigen.

Alternatively, the kits of the invention can be used to screen agents to determine their level of anti-chlamydial activity for skin and or keratinocyte infection and efficacy in treating a CTCL. For example a kit can comprise various known (control) and test agents, and any agents developed in the future for which anti-chlamydial activity for skin infection is to be determined. For an in vitro screening kit, the kit can comprise cultured human keratinocytes grown under appropriate conditions for testing agents, such as under serum free conditions. In addition, the kit could also be comprised of agents for detecting a *C. pneumoniae* protein, a *C. pneumoniae*-associated antigen, or a *C. pneumoniae* nucleic acid in a biological sample and means for determining the amount of the *C. pneumoniae* protein, *C. pneumoniae*-associated antigen, or *C. pneumoniae* nucleic acid (e.g., an antibody that binds a *C. pneumoniae* protein or a *C. pneumoniae*-associated antigen, or a nucleic acid probe that binds to a nucleic acid encoding a *C. pneumoniae* protein or *C. pneumoniae*-associated antigen in order to determine anti-chlamydial activity of the test agent. The instructional material included in a kit of the invention can be a publication, a recording, a diagram, or any other medium of expression that can be used to communicate one or more of the steps of any analytical, diagnostic, or therapeutic method included in the present invention. The instructional material can also include any medium of expression that is used to communicate the parameters within that to perform the steps of a method of the invention, and troubleshooting indications and precautions as would be obvious to one skilled in the art after reading the present disclosure. The instructional material of a kit included in the invention may comprise a plurality of materials that can be provided with one or more components of the kit. By way of example, a kit that is useful for diagnosing a form of CTCL in human patient may include an instructional material that outlines the method of diagnosing a CTCL in a mammal as described herein. Kits described herein can also include instructions for observing that a mammal to be tested is suffering from or is at risk of developing a disorder associated with aberrant expression fo a *C. pneumoniae*-associated antigen if the amount of the *C. pneumoniae*-associated antigen or mRNA encoding the *C. pneumoniae*-associated antigen is above or below a normal level.

For antibody-based kits, the kit can comprise, for example: (1) a first antibody (e.g., attached to a solid support) that binds to either a *C. pneumoniae* protein or a *C. pneumoniae*-associated antigen; and, optionally, (2) a second, different antibody that binds to either a *C. pneumoniae* protein, a *C. pneumoniae*-associated antigen, or the first antibody, and is conjugated to a detectable agent.

Anti-*C. pneumoniae* protein antibodies include those reacting with a major outer membrane protein. An antibody reactive with a *C. pneumoniae*-associated antigen would include those reactive with SAF, which as described herein would be an antibody binding to a 28 to 30 kDa protein that co-localizes with Chlamydial outer membrane protein (OMP) and lipopolysaccharide (LPS) in infected tissue and cell cultures and reacts with bacterial bodies as detected by electron microscopy.

For nucleic acid-based kits, the kit can comprise, for example: (1) a nucleic acid probe, e.g., a detectably labeled nucleic acid probe, that hybridizes to one of a *C. pneumoniae* nucleic acid sequence and portion of a gene sequence encoding a *C. pneumoniae* nucleic acid sequence and a portion of a gene sequence encoding *C. pneumoniae*-associated antigen. The kit can also comprise, e.g., a buffering agent, a preservative, a protein stabilizing agent, or components necessary for detecting the detectable (i.e. identifying) agent, such as an enzyme or a substrate. The kit can further comprise a control sample or a series of control samples that can be tested and compared to a test sample obtained from a mammal or from a cultured cell population. Each component of a kit may be enclosed within an individual container and all of the various containers may be within a single package, or may optionally be shipped separately.

A detectable labeled nucleic acid probe would be an oligonucleotide or PCR product generated using primers described herein, that is labeled with digoxigenin or with a fluorophor, such as fluoroscein isothiocyanate (FITC), well known to one skilled in the art.

The invention also includes a kit comprising an instructional material that outlines, describes, or illustrates a method of the present invention, and a pharmaceutical composition comprising an anti-chlamydial agent along with a delivery device for delivering the composition to a subject. By way of example, the delivery device may be a squeezable spray bottle, a metered-dose spray bottle, an aerosol spray device, an atomizer, a dry powder delivery device, a self-propelling solvent or powder-dispensing device, a syringe, a needle, or a dosage measuring container.

Each of the components of a kit described herein can be promoted, distributed, or sold either as a unit or as separate components to be used cooperatively. By way of example, the instructional material can be affixed to a container that contains one or more analytical, diagnostic, or therapeutic components useful in the methods described herein, or the instructional material can be shipped together with one or more containers that individually contain one or more of these components. By way of alternative example, the instructional material may be shipped separately from the method components with the intention that the instructional material and the components be used cooperatively by the recipient.

A kit provided by the invention can be useful for performing the methods of the invention, such as detecting and treating a *C. pneumoniae* infection in a mammal, such as a human, and diagnosing and treating a cutaneous T-cell lymphoma, such as mycosis fungoides or Sézary syndrome, in a mammal, such as a human or screening news agents for the treatment of *C. pneumoniae* infection in the skin of a mammal, such as a human.

The invention is now described with reference to the following examples. Examples are provided for the purpose of illustration only, and the invention is not limited to examples, but rather encompasses all variations that are evident as a result of the teaching provided herein.

EXAMPLES

The experiments presented in this examples demonstrate that the stimulatory factor, SAF, is present on *C. pneumoniae* organisms, and that SAF and *C. pneumoniae* antigens are present in lesions of certain CTCL patients, and that DNA and RNA of *C. pneumoniae* can be detected in CTCL patients. These experiments also demonstrate the effectiveness of PUVA therapy, and that keratinocytes are capable of being infected with *C. pneumoniae*, supporting the morphologic identification of infected keratinocytes in situ. The examples presented herein encompass Abrams et al. (1999, Clin. Diagnostic Lab. Immunol. 6:895–905), that is incorporated by reference as if set forth in its entirety herein.

The materials and methods of these examples are now described below.

Preparation of SAF

Proteins exhibiting SAF-like activity were recovered and purified from the SZ-4 cell line (Abrams et al., 1991, J. Investig. Dermatol. 96:31–37) in order to generate monoclonal antibodies (mAbs) that were inhibitory for SAF bioactivity. Conditioned medium (CM) from the SZ-4 cell line was generated as follows: SZ-4 cells were maintained in culture at 37° C. for 18 hours in RPMI-1640 culture media comprising one or more of 10% FBS, 1 microgram per milliliter of phytohemagglutinin (PHA, Sigma, St. Louis, Mo.), phorbol 12-myristate 13-acetate (TPA, Sigma, St. Louis, Mo.), and 1 millimolar per liter of Ionomycin (Sigma, St. Louis, Mo.). The treated cells were centrifuged, rinsed in media, and maintained for 72 hours in serum free RPMI-1640 culture media comprising Neutradoma HU (Boehringer Mannheim, Chicago, Ill.).

To characterize fractions for SAF-like activity, and to screen individual mAb clones for their ability to neutralize SAF activity, SAF bioassays were performed as previously described (Abrams et al., 1993, Can. Res. 53:5501–5506). Selected amounts of CM that had been incubated with SZ-4 cells were added to separate cultures of $1 \times 10^5$ peripheral blood mononuclear cells (PBMCs) maintained in 96-well flat pattern plates (Costar, Rochester, N.Y.) with RPM1–1640 culture media further comprising 10% FBS and 10 units per milliliter of recombinant IL-2 (rIL-2). These PBMCs were obtained from healthy donors (American Red Cross, Miami, Fla.) and were determined by the Red Cross to be sero-negative for HIV-1, HBV, and HTLV. The PBMCs were maintained in CM for 72 hours in a humidified 5% $CO_2$ incubator. At 68 hours of incubation time, 1 microCurie of tritiated thymidine ($^3$H-TdR) (Amersham, Arlington Heights, Ill.) was added to each well. The incubation was terminated by harvesting the PBMCs onto filter mats (Schleicher & Schuell, Keene, N.H.). The filter-bound cell material was then processed for liquid scintillation counting (LSC) by drying filter mats and adding 3 milliliter liquid scintillation fluid (Econofluor, Dupont/NEN, Wilmington, Del.).

Preparation of Anti-SAF mAb

CM containing SAF was semi-purified by anion exchange chromatography using a DE-52 anion exchange resin (Whatman, Clifton, N.J.). Anion exchange-purified CM was mixed with loading buffer comprising 2% sodium dodecyl sulfate (SDS) and 5% 2-mercaptoethanol such that the final concentration of CM was 50 units per 25 microliters of total volume. The resulting mixture was maintained at 55° C. for 10 minutes and electrophoresed according to the method of Laemmli (Laemmli, 1970, Nature (London) 227:680–685) through a 12% polyacrylamide gel matrix for 4 hours at a constant current of 25 milliamperes. Three one millimeter slices were excised from the gel, and the proteins from each gel slice were passively eluted into fresh culture media further comprising 10% FBS. The SDS in the eluted solution was removed by dialyzing the solution against 5 millimolar N,N-Bis[2 hydroxyethyl]-2-aminoethylsulfonic acid (BES), and the resulting dialysate was tested at various concentrations for SAF activity as described above.

The relative mobility ($R_f$) value of each gel/protein fraction was used to determine the apparent molecular mass of SAF. The 28–30 kilodalton (kD) SAF active fraction was injected into Balb/C mice, and hybridomas were made. The mAbs generated by the hybridomas, that were reactive with the immunogenic fraction (i.e. the 28–30 kD fraction), were screened for SAF inhibitory activity using both the PBMC-derived SAF and SZ-4 cell line-derived SAF. One clone 58.19, an $IgG_3$, was selected and re-cloned, and is hereinafter referred to as anti-SAF.

The anti-SAF assay was performed as follows. Selected concentrations of purified mAb IgG, ranging from 0 to 100 micrograms per milliliter, were added to selected concentrations of PBMC-derived SAF and SZ-4 CM. The resulting mixtures were maintained in individual wells of a 96-well plate for 1 hour, at that time $1 \times 10^5$ PBMCs were added to each well. Cells were then subjected to a previously reported SAF bioassay (Abrams et al., 1993, Can. Res. 53:5501–5506). The specificity of any observed inhibition was examined for each mAb by assessing the ability of the mAb to inhibit T cell proliferation induced either by 1 microgram per milliliter of PHA, or by a combination of 1 nanogram per milliliter of TPA and 1 millimole per liter of Iononycin.

Infection of Cell Cultures with *C. pneumoniae*

Keratinocyte cell cultures were established either on glass chamber well slides (Lab-Tek) or in culture flasks. The keratinocyte cultures were allowed to reach 40–50% confluence, following that 200 IFU-50 per $cm^2$ culture area of *C. pneumoniae* (ATCC, Rockville, Md.) was added to the media. Following the infection, the flasks or well slides were centrifuged at 500×g for 30 minutes. Total culture volume was 2 milliliter for cultures in T-25 flasks and 200–400 microliters for cultures in well slides. After centrifugation, additional culture media was added to each culture to bring each of the well slide cultures to 2 milliliters total volume and each of the T-25 flask cultures to 7 milliliters total volume.

The non-adherent monocyte cell line, THP-1, described previously in Abrams et al. (1999, Clin. and Diag. Lab. Immunol. 6, pp. 895–905), was exposed to *C. pneumoniae* $2 \times 10^5$ cells per milliliter in T-25 standing flasks. THP-1 cultures were maintained for 72 hours, and cells were either treated for extraction of nucleic acids or prepared for immunohistochemistry. THP-1 cells were prepared for immunohistochemistry by cytocentrifugation onto ProbeOn Plus slides (Fisher Scientific, Pittsburgh, Pa.) using a Cytospin III (Shandon Instruments, La Jolla, Calif.) at 800 rotations per minute (rpm) for 5 minutes. The culture media was removed from each slide and cells were rinsed twice with Hanks buffer. The washed cells were fixed using Streck Tissue Fixative (S.T.F., Streck, Omaha, Nebr.). One milliliter of S.T.F. was added to each slide, and the slides were maintained at room temperature for 24 hours. Cytospun cells were fixed with S.T.F. in a Coplan jar for at least 1 hour.

Immunohistochemistry

Skin tissue obtained from 27 patients with cutaneous T cell lymphoma (CTCL) were used for immunohistochemistry studies. Formalin-fixed paraffin embedded sections were de-paraffinized using mixed xylenes and rehydrated in automation buffer (Biømeda, Foster City, Calif.). For immunohistochemical analysis of the sections, a modified version of a previously reported ABC technique was used (Hsu et al., 1981, Am. J. Clinic. Patrol. 75:816–21). The modification entailed the use of capillary gap ProbeOn® Plus slides (Fisher Scientific, Pittsburgh, Pa.) that have painted surfaces that create a 15 micrometer gap between the slides when placed face to face. This protocol uses reagents designed specifically for capillary gap slides, including an antibody diluting buffer (Biømeda, Foster City, Calif.).

Detection of *C. pneumoniae* Outer Membrane Protein (OMP) and Lipopolysaccharide (LPS) in Keratinocytes Fixed cells were exposed first to automation buffer (Biømeda, Foster City, Calif.), then to 3% aqueous hydrogen peroxide. A monoclonal antibody (mAb) directed to the *C. pneumoniae* OMP (Clone RR402, DAKO, Carpinteria, Calif.), and a genus specific mAb directed against the Chlamydial LPS (Imagen kit, DAKO, Carpinteria Calif.) were used as primary antibodies, and each was diluted 1:10 in antibody diluting buffer (Biømeda, Foster City, Calif.). Cells were incubated with, either primary or secondary antibody for 30 minutes and rinsed five (5) times with automation buffer. Primary and secondary antibody binding were detected using a super $ABC^{TN}$ kit (Biømeda, Foster City, Calif.) according to the manufacturer's instructions. Following the fifth rinse, and after exposure to the secondary antibody, peroxidase enhancer (Biømeda, Foster City, Calif.) was added for 1 minute. Antibody-antigen binding was visualized following incubation with Diaminobenzidine Cobalt Chromagen (Biømeda, Foster City, Calif.) for 6–8 minutes. Slides were rinsed with distilled water and counterstained for 1 minute with aqueous hematoxylin (Biømeda, Foster City, Calif.). Slides were covered with Crystal Mount™ (BiØmedia, Foster City, Calif.) and dried to room temperature for 2 hours. Dried slides were viewed using an Olympus BX-40 microscope and photographed using an Olympus SC-35 camera.

RNA Extraction

RNA extraction from cultures and the subsequent removal of media from the cultures was performed using an Ultraspec RNA kit (Biotecx, Houston, Tex.) as previously described (Nolte et al., 1994, J. Clin. Microbiol. 32:519–520). Following extraction, the RNA was incubated at 37° C. for 2 hours in a solution comprising 2 micrograms per milliliter RNase-free DNase and RNase-free water. The DNA-free RNA was isolated by adding 100 milliliter of RNA extraction buffer Ultraspec (Biotecx, Houston, Tex.) followed by 0.2 volumes of chloroform. All RNA preparations were run on a 1% SeaKem agarose gel (FMC, Rockland, Me.) and examined by ethidium bromide incorporation for the presence of 28S and 18S ribosomal RNA (rRNA).

RT-PCR

The double stranded cDNA used for PCR analysis (RT-PCR) was generated as follows. A 1–2 microgram sample of RNA was mixed with 1 microliter of a solution comprising 0.5 milligrams of oligo dT (Perkin Elmer, Foster City, Calif.), 6 microliters of a solution comprising a 5 times (5×) concentrated reaction buffer (Life Technologies, Grand Island, N.Y.), 1.5 microliters of each dNTP (Perkin-Elmer, Foster City, Calif.), a solution comprising 0.6 microliters of RNasin (Promega, Madison, Wis.), and a solution comprising 2 microliters of reverse transcriptase (Life Technologies, Grand Island, N.Y.). The mixture was brought to a final volume of 30 microliters by adding RNase free water, centrifuged for 5 seconds, and maintained for 1.5 hours at 37° C. The MuLV-reverse transcriptase was activated by incubating the final mixture at 95° C. for 3 minutes. The double stranded cDNA produced using this procedure was stored at −20° C. Approximately 2–4 microliters of this cDNA was used for each of the subsequent PCR reactions.

Preparation of DNA for PCR

DNA was extracted from cultured keratinocytes as follows. The cultures were washed with 5 milliliters Hank's Buffered Saline Solution (HBSS) further comprising 5 millimolar HEPES. Five milliliters of a DNA lysis buffer comprising 25 millimolar Tris pH 8.0, 100 millimolar NaCl, 10 millimolar EDTA, and 0.5% SDS was added to each flask of cells. For DNA extraction from patient tissue samples, frozen specimens were homogenized in the lysis buffer. The DNA obtained from cultured cells and patient tissue were afterward treated identically. The DNA-containing lysates from either cultures or tissue were maintained at 37° C. for 1 hour, and 12 milliliters of a solution comprising 20 milligrams per milliliter of proteinase K (Life Technologies, Grand Island, N.Y.) was added. The mixture was incubated at 37° C. for 2 hours. Following centrifugation at 1500×g for 10 minutes, the mixture was transferred to a different tube, and DNA was extracted from the mixture using the "hot phenol" method previously described (Balin et al., 1998, Med. Microbiol. Immunol. 187:23–42). The aqueous phase from the extraction was mixed with 2.5 volumes of 100% ethanol and 0.1 volumes of a solution comprising 3 molar sodium acetate, and maintained overnight at room temperature. The resulting solution was centrifuged at 10,000×g for 30 minutes. The DNA pelleted during centrifugation was air-dried and suspended in TE buffer having a pH of 8.5 and comprising 0.05 M Tris and 0.005 M EDTA. The DNA solutions prepared in this manner were stored at −20° C., and quantitated by UV absorption analysis (A260/A280) using a Spectrophotometer 610. Aliquots of these stored solution comprising 0.1 micrograms of DNA were used in subsequent PCR reactions.

PCR

PCR was designed as follows. A reaction solution comprising Buffer II with magnesium chloride ($MgCl_2$), 1.25 units of AmpliTaq DNA polymerase (Perkin Elmer), 200 micromoles per liter of each of the four deoxynucleotide bases (dNTPs), 20 picomoles of each primer and either one aliquot of DNA (i.e. 0.1 micrograms DNA), 2 microliters of cDNA, or 2 microliters of PCR product (i.e. for nested PCR reactions). Each reaction mixture was brought to a final volume of 50 microliters by adding water. External and internal nested primers were used for detection of *C. pneumoniae* DNA and cDNA omp-A gene and 16S rRNA gene sequences in cultures infected with TW-183. The Omp-A primer sequences and nucleotide position numbers were obtained from GenBank accession number M64064, and all sequences are listed 5'-3' as follows: omp-A-external plus strand primer nucleotides 281–300, omp-A-external minus strand nucleotides 1073–1053, omp-A internal primer plus strand nucleotides 390–411, and omp-A internal primer minus strand nucleotides 730–711 (i.e. omp-A primer set 1, 340 nucleotide separation). Primers and nucleotide sequences for 16S rRNA gene were determined from GenBank accession number L06108 (Gays et al., 1993, Int. J. Cyst. Bacteriol. 43:610–612). The 16S rRNA primer sequences are all follows: external plus strand nucleotides 71–90, external minus strand nucleotides 1465–1446, internal plus strand nucleotides 243–266, and minus strand nucleotides 976–953.

PCR conditions were as follows. Reactions comprising the 16S rRNA gene external primers for C. pneumoniae were denatured for 5 minutes at 94° C., and subjected to 35 cycles of denaturing, annealing, and elongation comprising, 30 seconds at 94° C., 30 seconds 48° C., and 1 minute at 72° C. PCR reactions were concluded by maintaining the reaction for 5 minutes at 72° C. Reactions comprising the 16S rRNA internal primer were performed in the manner described for reactions comprising the external primers except that the annealing conditions in each cycle were 68° C. for 30 seconds. Reactions comprising the omp-A external primer of C. pneumoniae were denatured by heating the reaction for 5 minutes at 94° C. The denatured reaction was subjected to 35 cycles of denaturing, annealing, and elongation respectively comprising 15 seconds at 94° C., 15 seconds at 56° C., and 15 seconds at 72° C. These reactions were concluded with a 7 minutes incubation at 72° C. Reactions comprising the omp-A internal primer were performed in the manner described for reactions comprising the external primers except that the annealing conditions for each cycle were 15 seconds at 59° C.

For detection of either RNA or DNA comprising the omp-A gene in patient tissue samples, the following sets of nested primers were employed: external primers corresponding to plus strand nucleotides 26–43 and minus strand nucleotides 567–548, and internal primers corresponding to plus strand nucleotides 115–135 and minus strand nucleotides 462–444 (Melgosa-Perez et al., 1991, Infect. Immun. 59:2195–2199). PCR conditions for these reactions were as follows: 35 cycles of 30 seconds at 95° C., 1 minutes at 52° C., and 1 minutes at 72° C. Nested PCR products generated in these reactions were electrophoresed in 1.8% agarose gels and visualized using ethidium bromide staining. All other PCR conditions were as described above for DNA and RNA obtained from cultured cells.

The PCR products generated using either infected cultured cell DNA or patient tissue DNA were cloned into a pcDNA vector using a TA cloning kit (Invitrogen, Carisbad, Calif.). Sequencing of the plasmid DNA confirmed the identity of these PCR products as gene sequences corresponding to either the omp-A gene or the 16S rRNA gene.

Ultrastructural Analysis

Negative staining immunoelectron microscopy was performed as follows. A liquid sample comprising either cultured keratinocytes or cells obtained from a human patient, and having a volume of about 5–10 microliters, was adsorbed onto carbon-coated copper electron microscope (EM) grids, and the grids were rinsed with a solution comprising PBS. The rinsed grids were blocked by treatment with a solution comprising 0.1% cold water fish gelatin and PBS for 10 minutes. The grids were then exposed to one or more primary antibodies, i.e. anti-LPS (1:20), anti-OMP (1:5), and anti-SAF (1:100), for about 15 minutes at room temperature. The grids were re-blocked by exposure to the solution comprising 0.1% cold water fish gelatin and PBS, rinsed again with PBS, and exposed for 30 minutes to a solution comprising 1 milligram per milliliter of a secondary anti-mouse antibody conjugated to 5–10 nanomoles of colloidal gold particles. The grids were rinsed with double distilled water and negative stained by treatment with a solution comprising 2.0% uranyl acetate. The grids were then examined at 80 kilovolts (kV) on a Zeiss EM-10 electron microscope.

The results of the experiments presented in these Examples are now described below.

Results

Figure 2:
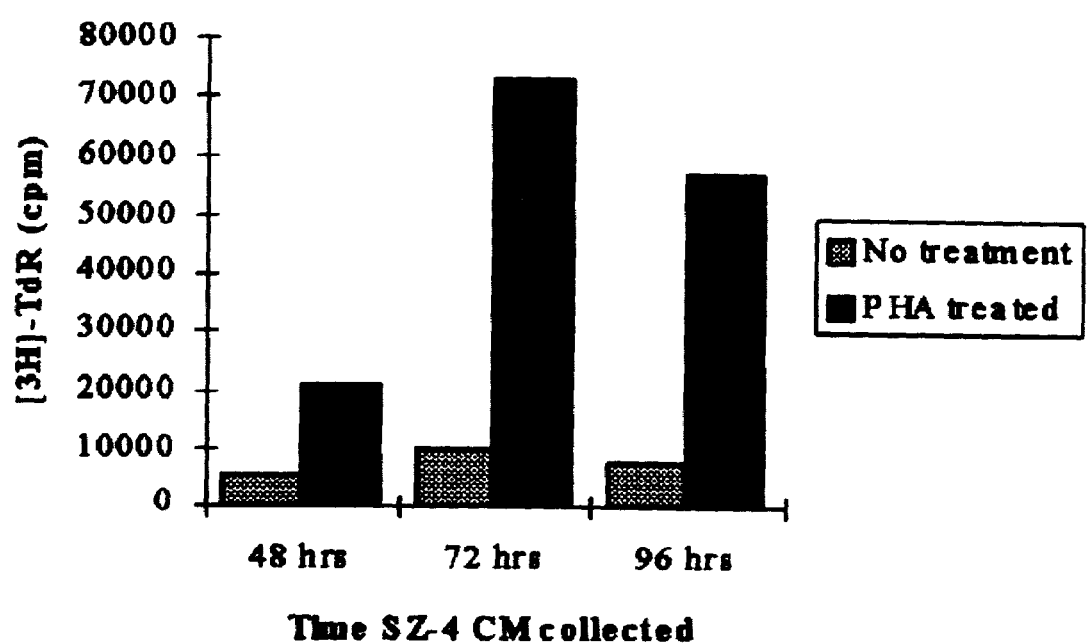
FIG. 2 is a graph depicting SAF production by a malignant clonal T cell line. Sezary 4 cells were exposed to PHA 1 mg/ml (black column) or media (hatched column) overnight and then cultured for 48, 72, or 96 hours. Conditioned media were collected and tested for induction of proliferation on a quiescent Sezary T cell line. No conditioned media response was 14,600 cpm.
Figure 3A:
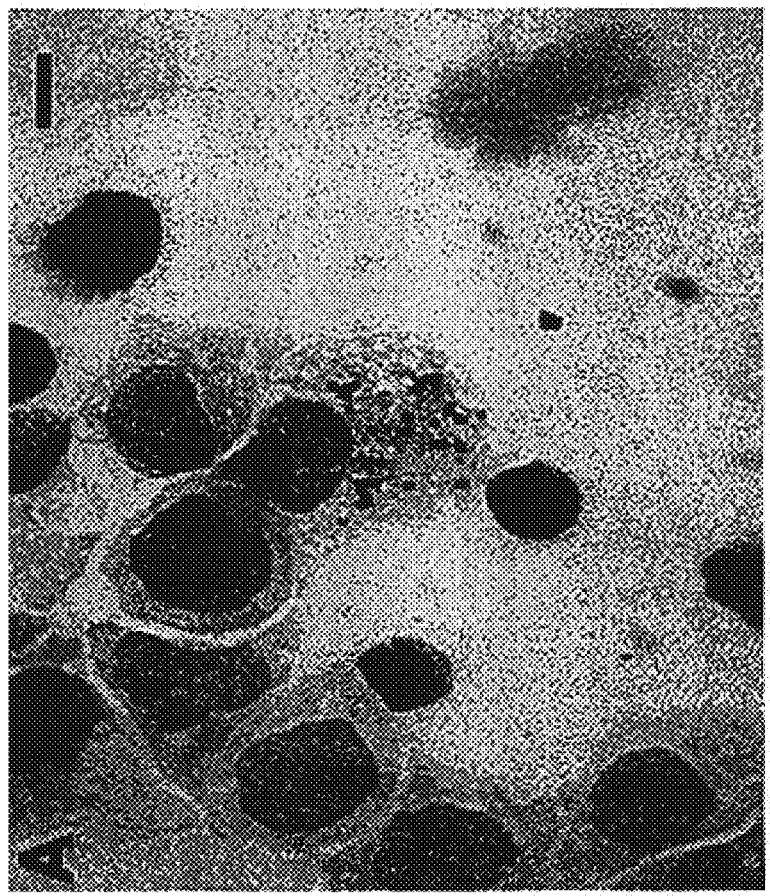
FIG. 3A is an image depicting immunolabeling of THP-1 cells, infected with *C pneumoniae* isolated from the brain of an AD patient using anti-OMP antibody. Cultured THP-1 cells were placed on slides using cytospin, and the cells were then fixed using STF®. The image demonstrates immunolabeling of bacterial inclusions using anti-OMP. The bar indicates 10 micrometers.
Figure 3B:
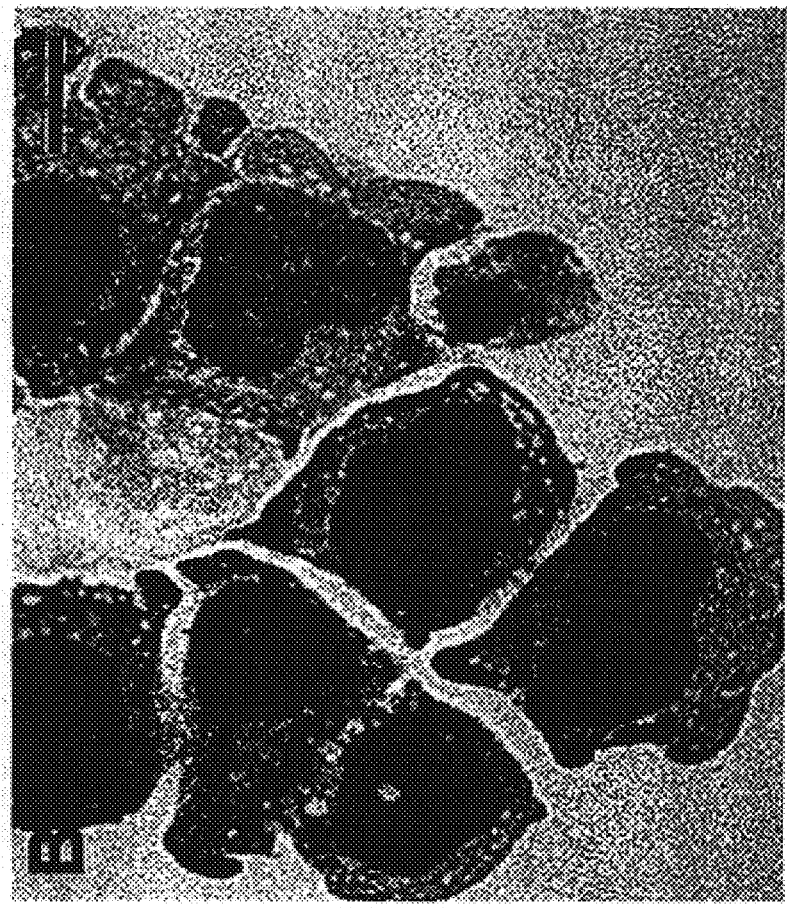
FIG. 3B is an image depicting the lack of immunolabeling of uninfected THP-1 cells exposed to anti-SAF antibody (i.e., the negative control).
Figure 3C:
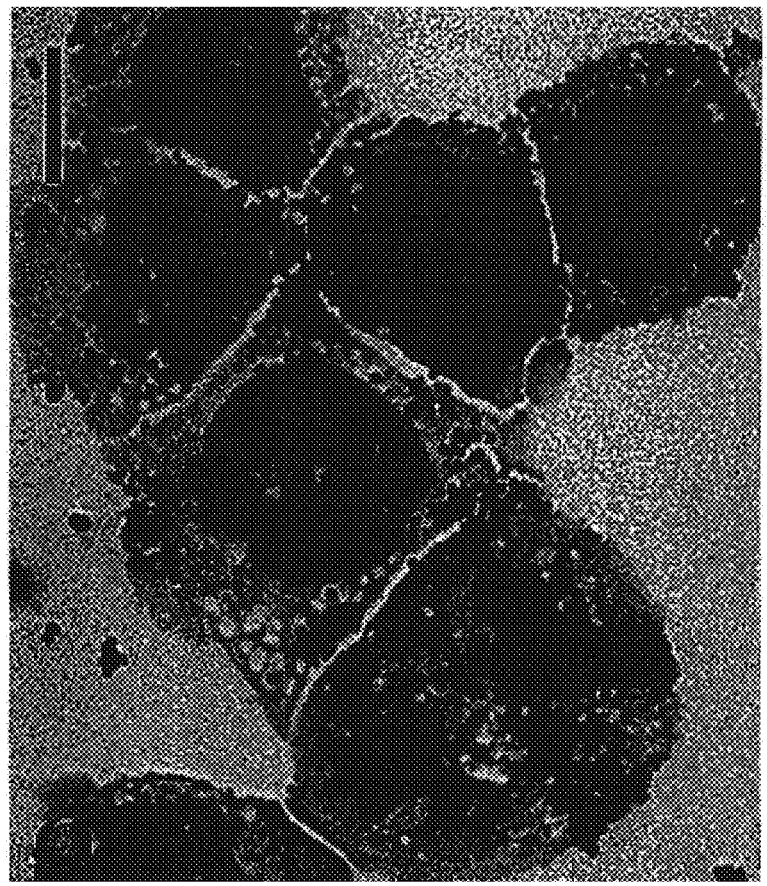
FIG. 3C is an image depicting immunolabeling of THP-1 cells, infected with *C pneumoniae* isolated from the brain of an AD patient using anti-SAF antibody. Cultured THP-1 cells were placed on slides using cytospin, and the cells were then fixed using STF®. The image demonstrates immunolabeling of bacterial inclusions using anti-SAF. The bar indicates 10 micrometers.
Figure 3D:
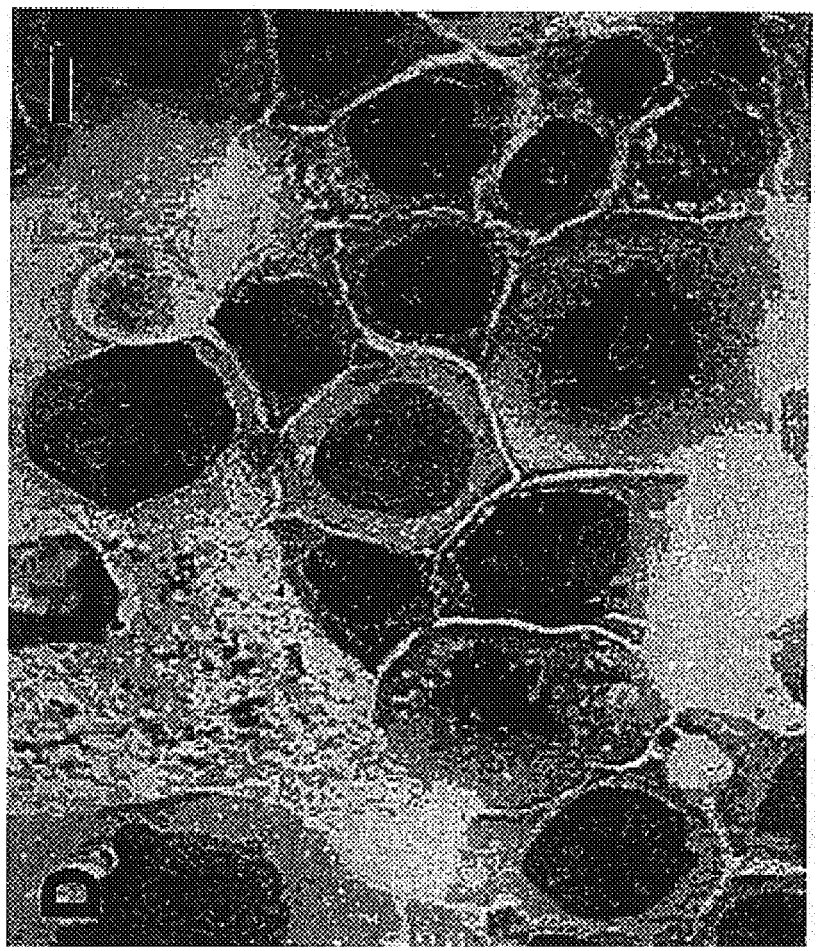
FIG. 3D is an image depicting immunolabeling of THP-1 cells, infected with *C pneumoniae* isolated from the brain of an AD patient using anti-LPS antibody. Cultured THP-1 cells were placed on slides using cytospin, and the cells were then fixed using STF®. The image demonstrates immunolabeling of bacterial inclusions using anti-LPS. The bar indicates 10 micrometers.

SAF is a 28–30 kDa protein with the ability to stimulate CTCL malignant cell growth (Abrams et al., 1993, Can. Res. 53:5501–5506). It has been previously reported that SAF can be produced by cells within the PBMCs of patients with Sézary syndrome and can be used to establish cell lines containing the predominant T cell clone (Abrams et al., 1991, J. Investig. Dermatol. 96:31–37; Abrams et al., 1991, J. Immunol. 146:1455–1462). One of these lines (SZ-4) was shown to produce detectable amounts of SAF (Abrams et al., 1991, J. Investig. Dermatol. 96:31–37). Monoclonal antibodies reactive against SAF derived from both PBMCs and the SZ-4 cell line were selected for their ability to neutralize SAF activity. The biological specificity of the selected mAb(anti-SAF) is demonstrated in FIG. 1. Anti-SAF was tested against either PHA, or TPA and Ionomycin stimulation, SZ-4 cell line-derived-SAF, or PBMC-derived-SAF (SZ-1). No inhibition of the PHA or TPA and Ionomycin response was observed, demonstrating that the antibody does not inhibit proliferation through toxicity or non-specific cell surface interactions. However, the antibody inhibits about 50% of both the cell line- and PBMC-derived SAF induced proliferation. The PBMCs and SZ-4 cell lines were both derived from patients with Sézary syndrome. FIG. 2 illustrates the production of SAF-like activity by the SZ-4 cell line in both a constitutive (hatched column) and inducible (black column) manner.

Figure 6A:
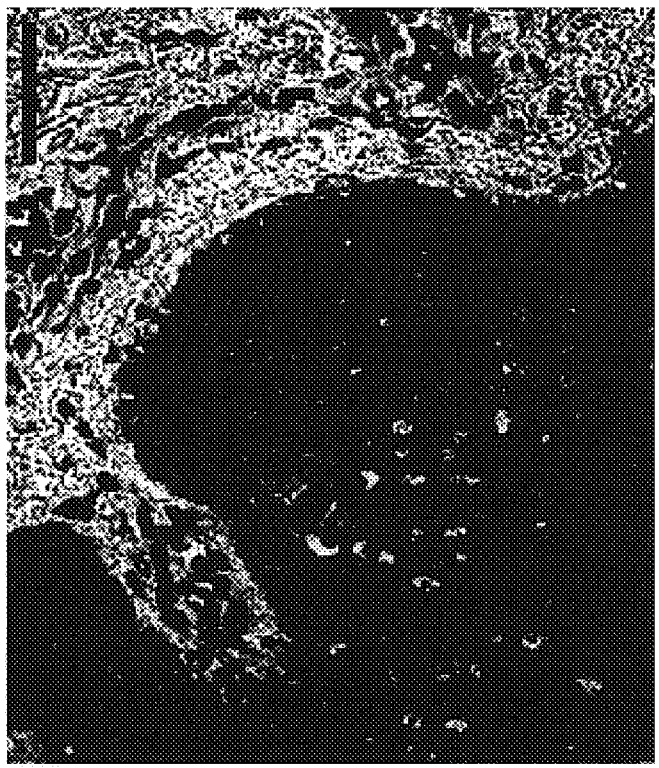
FIG. 6A is an image depicting the effect of combined psoralen-ultraviolet radiation (PUVA) therapy on *C. pneumoniae* SAF antigen expression. Immunolabelling of formalin-fixed sections from biopsies obtained before PUVA therapy using anti-SAF antibody is depicted. The image demonstrates that epidermal and dermal cells immunolabelled using anti-SAF exhibit a diffuse and highly localized pattern not observed in the section immunostained after PUVA treatment (FIG. 6D). The tissue depicted was stained using diamino benzidene (DAB)-Cobalt chromagen. The bar indicates 50 micrometers. The bar in the figure indicates 50 micrometers.
Figure 6B:
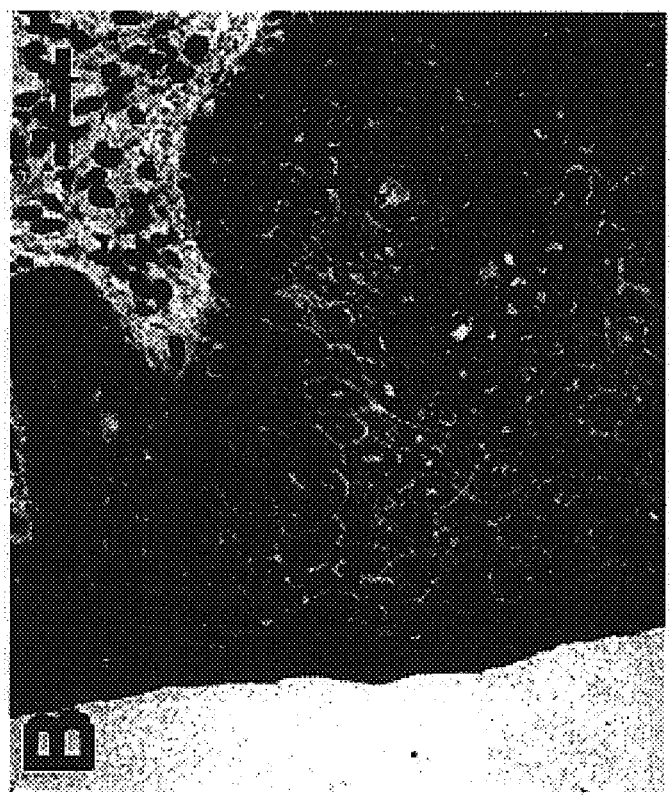
FIG. 6B is an image depicting the effect of combined psoralen-ultraviolet radiation (PUVA) therapy on *C. pneumoniae* OMP antigen expression. Immunolabelling of formalin-fixed sections from biopsies obtained before PUVA therapy using anti-OMP antibody is depicted. The image demonstrates that epidermal and dermal cells immunolabelled using anti-OMP exhibit a highly localized pattern (indicated by arrows), that is not observed in the section immunostained after PUVA treatment (FIG. 6E). The bar in the figure indicates 50 micrometers.
Figure 6C:
FIG. 6C is an image depicting the effect of combined psoralen-ultraviolet radiation (PUVA) therapy on *C. pneumoniae* LPS antigen expression. Immunolabelling of formalin-fixed sections from biopsies obtained before PUVA therapy using anti-LPS antibody is depicted. The image demonstrates that cells immunolabelled using anti-LPS exhibit an intense, diffuse and localized staining pattern not observed in the corresponding post-PUVA immunostained section (FIG. 6F). The bar in the figure indicates 50 micrometers.

To determine whether SAF expression can be detected within the skin of patients with mycosis fungoides, the predominant form of CTCL, sections from formalin-fixed biopsies obtained from lesions of patients with mycosis fungoides were labeled with anti-SAF. Sections from sixteen of 27 patients were reactive with the anti-SAF antibody. Typical results of these experiments are depicted in FIGS. 6A through 6C. Interestingly, reactivity was found within keratinocytes within the epidermis and in endothelial cells and histiocytes within the dermis as illustrated by the micrograph image in FIG. 6A. Sections from the remaining 11 patients showed little or no immunoreactivity, suggesting that the immunolabelling was specific.

In consideration of whether SAF reactivity observed in the skin is predictive of OMP and LPS reactivity in this tissue, immunocytochemistry was performed on sections made from the same biopsies analyzed above using commercially available mAbs specific for C. pneumoniae OMP and Chlamydial LPS. As shown in FIG. 6B, the anti-OMP reactivity in consecutive sections was highly localized, appearing to specifically stain inclusions within keratinocytes and histiocytes. In contrast, FIG. 6C depicts a reactivity pattern of both diffuse and highly localized staining observed for the anti-LPS. As the photomicrographic image in FIG. 6C depicts, keratinocytes, endothelial cells, and histiocytes demonstrate both diffuse and intense focal immunoreactivity. Interestingly, anti-OMP staining also demonstrated diffuse immunoreactivity in some samples obtained from patients with more advanced disease. In a series of 27 specimens tested, immunoreactivity was found in approximately 60% of the specimens with 90% concordance between reactivity of the anti-SAF, anti-LPS, and anti-OMP mAbs. Thus, SAF appears to immunolabel C. pneumoniae bacteria.

To test directly whether SAF is expressed by C. pneumoniae, the expression of the anti-OMP, anti-LPS and anti-SAF antibodies on macrophage cell line cultures (THP-1) infected with either the laboratory strain of C. pneumoniae (TW-183) or C. pneumoniae isolated from the brains of AD patients (Balin et al., 1998, Med. Micro. & Immunol. 187:23–42) was analyzed. The identity of the associated AD bacterium as C. pneumoniae was confirmed by PCR, RT-PCR, ultrastructural, and cell culture analyses as described above (Balin et al., 1998, Med. Micro. & Immunol. 187: 23–42). Immunohistochemistry demonstrated that 7-day cultures infected with AD-isolated organisms all showed a similar reactivity pattern. As shown in FIGS. 3A–D, respectively, reactivity of the anti-OMP, anti-SAF on uninfected cells (negative control), anti-SAF on infected cells, and anti-LPS, clearly demonstrated that these antibodies reacted with the bacteria infecting the macrophages. Anti-SAF clearly reacted with bacteria, but did not show any of the diffuse staining observed in the tissues. The anti-LPS had both diffuse and more focused staining. These staining patterns presumably represent differences in the antigenic profiles between these two isolates of C. pneumoniae and demonstrate differential labeling for more persistent infections (i.e., 7 days vs. 11 days). These results suggest that SAF is a protein directly associated with C. pneumoniae infection.

Figure 4A:
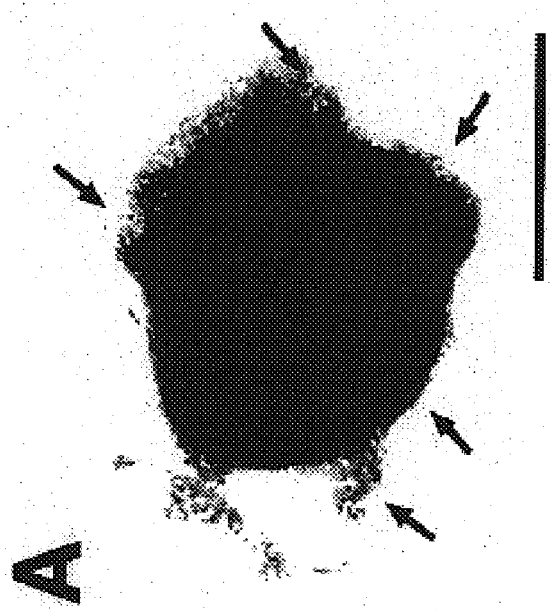
FIG. 4A is an image depicting negative staining combined with immuno-electron microscopy of *C. pneumoniae* using anti-SAF antibody. THP-1 (a monocyte cell line) cells were infected with *C. pneumoniae* isolated from a patient with AD, and cultured for 7 days. Pellets were prepared from infected cell culture supernatants, and the pelleted material was adsorbed onto carbon-coated copper EM grids. The grids were exposed to and incubated with mouse anti-SAF antibody followed by incubation with secondary anti-mouse antibody conjugated to 5 nanometer colloidal gold particles (i.e., immunogold). The image depicts immunogold particles (indicated by arrows) bound to an anti-SAF-labeled bacterium. The bar indicates 0.75 micrometers.
Figure 4B:
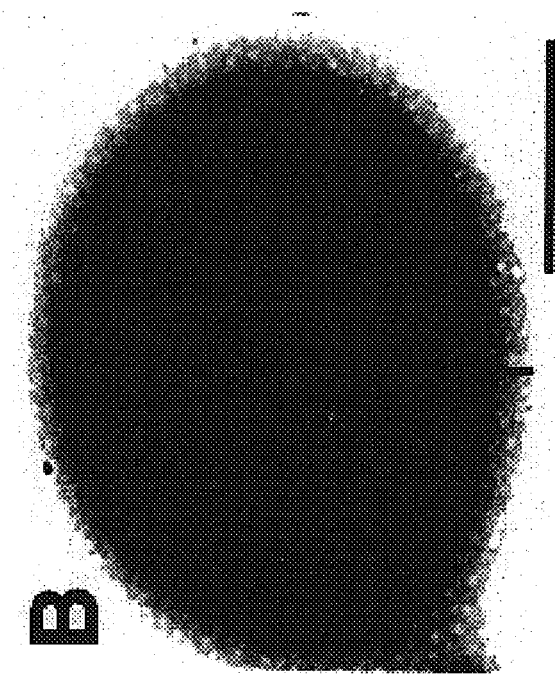
FIG. 4B is an image depicting negative staining combined with immuno-electron microscopy of *C. pneumoniae* using anti-OMP antibody. THP-1 (a monocyte cell line) cells were infected with *C. pneumoniae* isolated from a patient with AD, and cultured for 7 days. Pellets were prepared from infected cell culture supernatants, and the pelleted material was adsorbed onto carbon-coated copper EM grids. The grids were exposed to and incubated with mouse anti-OMP antibody followed by incubation with secondary anti-mouse antibody conjugated to 5 nanometer colloidal gold particles. The image depicts immunogold particles (indicated by arrows) bound to a bacterium apparently rich in OMP protein. The bar indicates 0.5 micrometers.
Figure 4C:
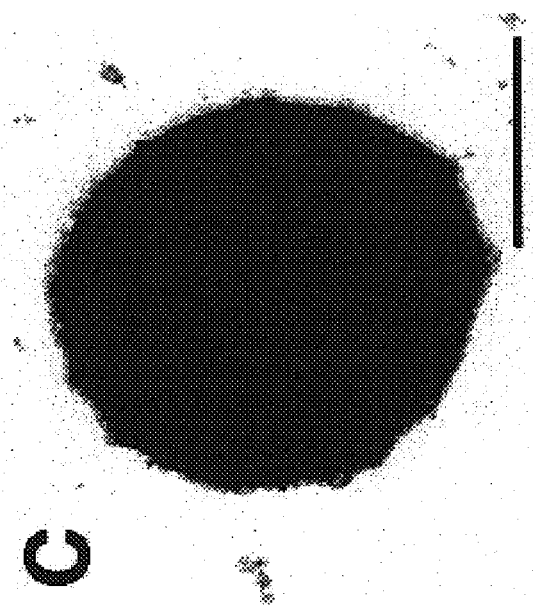
FIG. 4C is an image depicting negative staining combined with immuno-electron microscopy of *C. pneumoniae* using anti-LPS antibody. THP-1 (a monocyte cell line) cells were infected with *C. pneumoniae* isolated from a patient with AD, and cultured for 7 days. Pellets were prepared from infected cell culture supernatants, and the pelleted material was adsorbed onto carbon-coated copper EM grids. The grids were exposed to and incubated with mouse anti-LPS antibody followed by incubation with secondary anti-mouse antibody conjugated to 5 nanometer colloidal gold particles. The image depicts heavy surface labelling of a bacterium by immunogold particles (indicated by arrows). The bar indicates 0.5 micrometers.

To determine if SAF is localized on C. pneumoniae, immunoelectron microscopy was performed. C. pneumoniae was reacted with anti-SAF or anti-OMP followed by 5 nanomoles gold-conjugated goat anti-mouse antibodies. As shown in FIGS. 4A, 4B, and 4C, respectively, immunoelectron microscopy confirmed that anti-SAF, anti-OMP, and anti-LPS specifically label C. pneumoniae.

Figure 5A:
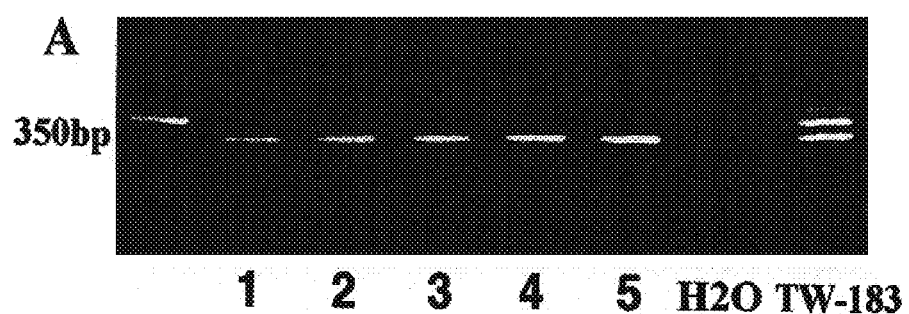
FIG. 5A is an image of a gel depicting a PCR analysis specific for *C. pneumoniae* using DNA obtained from patients with CTCL. A nested primer set specific for the omp-A gene of *C. pneumoniae* (i.e., omp-A primer sequence ID 1–4, see Methods) was used. The image depicts the amplification products obtained using DNA extracted from the skin of 5 patients with mycosis fungoides (lanes 1–5) that was subjected to a polymerase chain reaction (PCR). The image depicts that the predicted 350 base pair amplification product was detected in the samples. A PCR reaction containing only water in the absence of primers served as the negative control. The positive control was the PCR product obtained using DNA obtained from the TW-183 lab strain of *C. pneumoniae*. Three bands were detected in the positive control, including a band at about 350 bp, that is the expected size of the amplification product.

If the detection of C. pneumoniae antigens in skin lesions of CTCL patients is a result of C. pneumoniae infection, it should be possible to detect C. pneumoniae specific DNA sequences by PCR in lesions of CTCL patients as well. Accordingly, DNA was isolated from skin samples of 5 patients with mycosis fungoides. PCR was performed with nested omp-A specific C. pneumoniae specific PCR primer pair as described above. As shown in FIG. 5A, PCR was found to be positive for all 5 of these preparations. The PCR pattern with the positive control DNA contained some additional bands of unknown origin that were not found in CTCL DNA preparations. These data suggest that our results were not a spurious outcome of DNA contamination from the positive control extractions; a conclusion supported also by water controls that were consistently negative. The PCR data, therefore, are consistent with the immunohistochemical data.

If SAF expression is associated with an active C. pneumoniae infection, then C. pneumoniae RNA encoding the omp-A gene product should be detectable in at least some patients with CTCL. RNA was isolated from lymph node biopsies from 5 patients, two with mycosis fungoides and 3 with Sézary syndrome. RT-PCR was performed with the omp-A -specific primers on the DNase treated RNA. As shown in FIG. 5B, the appropriate 350 bp product was detected in 3 of 5 samples, one with mycosis fungoides and two with Sézary syndrome. These data suggest that omp-A is actively transcribed in certain patients with CTCL. To ensure that these PCR products contain C. pneumoniae-related sequences, we isolated, cloned, and sequenced the 350 bp product and found it to be identical to the predicted sequence as described (Melgosa-Perez et al., 1991, Infect. Immun. 59:2195–2199). These results were consistent with our PCR and immunohistochemical data indicating that at least some patients with CTCL are infected with transcriptionally active C. pneumoniae.

Figure 6D:
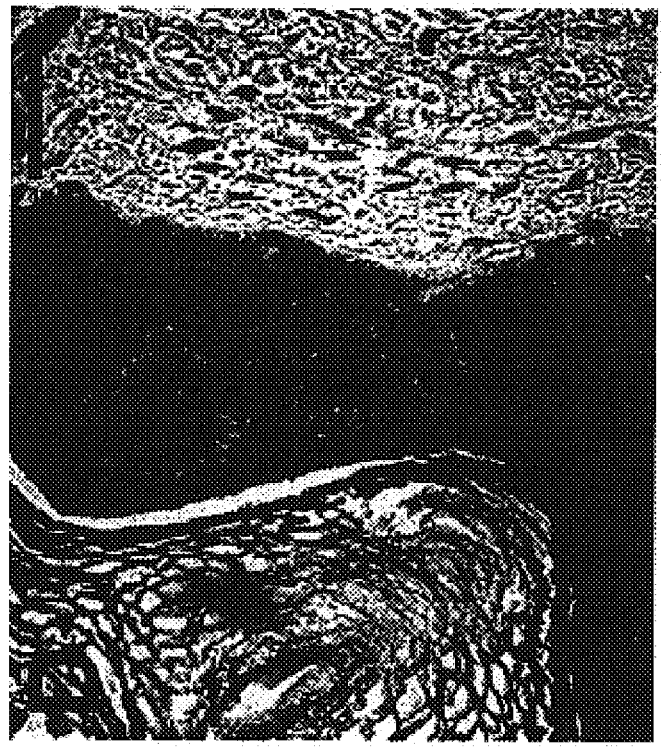
FIG. 6D is an image depicting the effect of combined psoralen-ultraviolet radiation (PUVA) therapy on *C. pneumoniae* SAF antigen expression. The image depicts immunolabelling of formalin-fixed sections from biopsies obtained after PUVA therapy using anti-SAF antibody. The image demonstrates that cells incubated with anti-SAF after PUVA treatment were not labelled as was observed in pre-treatment sections (FIG. 6A). The bar in the figure indicates 50 micrometers.
Figure 6E:
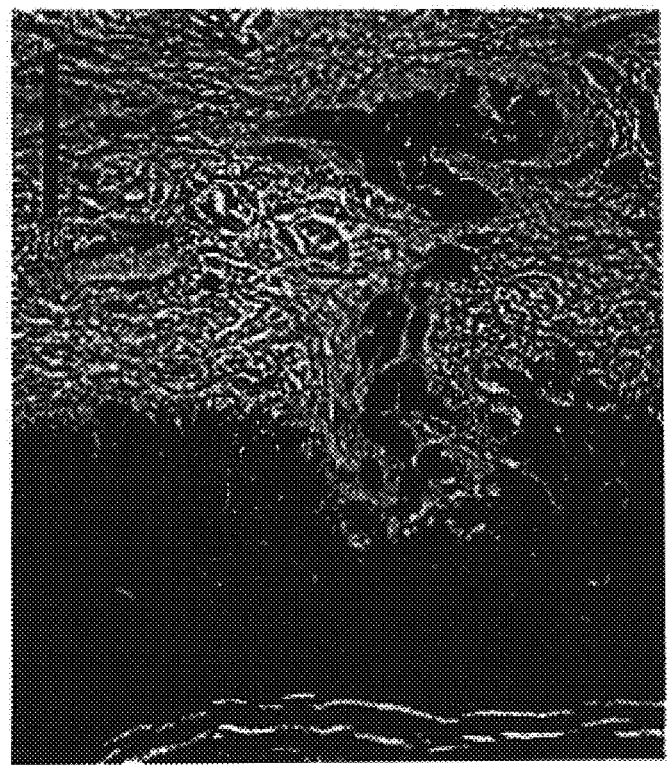
FIG. 6E is an image depicting the effect of combined psoralen-ultraviolet radiation (PUVA) therapy on *C. pneumoniae* OMP antigen expression. The image depicts immunolabelling of formalin-fixed sections from biopsies obtained after PUVA therapy using anti-OMP antibody. The image demonstrates that cells incubated with anti-OMP after PUVA treatment were not labelled in contrast to the immunolabelling observed in pre-treatment sections (FIG. 6B). The bar in the figure indicates 50 micrometers.
Figure 6F:
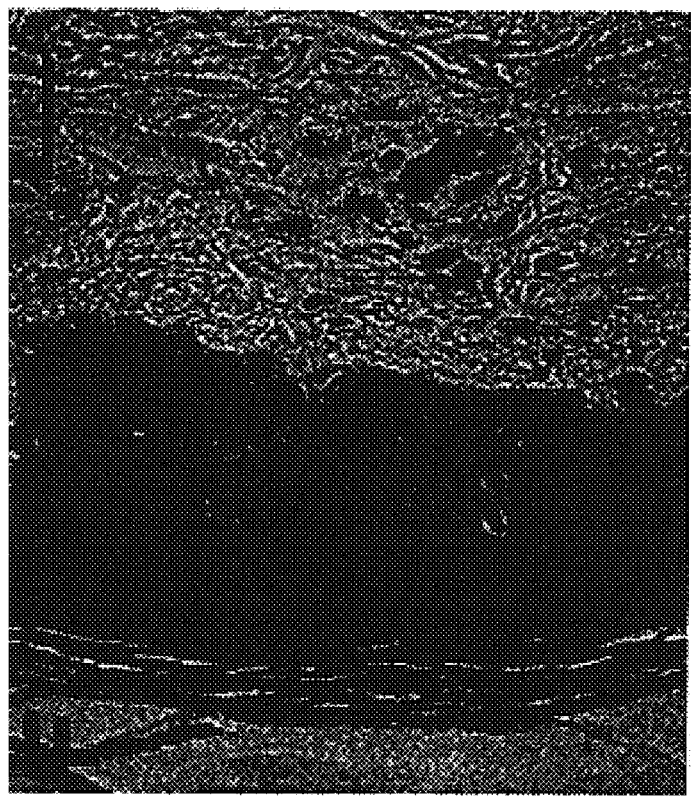
FIG. 6F is an image depicting the effect of combined psoralen-ultraviolet radiation (PUVA) therapy on *C. pneumoniae* LPS antigen expression. The image depicts immunolabelling of formalin-fixed sections from biopsies obtained after PUVA therapy using anti-LPS antibody. The image demonstrates that cells incubated with anti-LPS after PUVA treatment were not immunolabelled compared with the staining observed in pre-treatment sections (FIG. 6C). The bar in the figure indicates 50 micrometers.

To initially evaluate the relationship between active CTCL and the expression of SAF, OMP, and LPS, biopsies from 4 patients were obtained from sites in close proximity pre- and post PUVA treatment. Immunocytochemistry was performed with the anti-LPS, anti-SAF, and anti-OMP mAbs on these identically processed specimens. Immunoreactivity for all of these antigens was greatly diminished after therapy. FIG. 6 demonstrates results from one of these patients at pre-treatment, shown in FIGS. 6A–6C, and at post-treatment, shown in FIGS. 6D–6F. FIGS. 6A and 6D depict anti-SAF reactivity, FIGS. 6B and 6E depict anti-OMP reactivity, and FIGS. 6C and 6F depict anti-LPS reactivity. These micrograph images clearly demonstrate that the staining in the pretreatment specimens is specific, and indicates that SAF and the expression of other C. pneumoniae encoded gene products are associated with active CTCL.

Figure 7A:
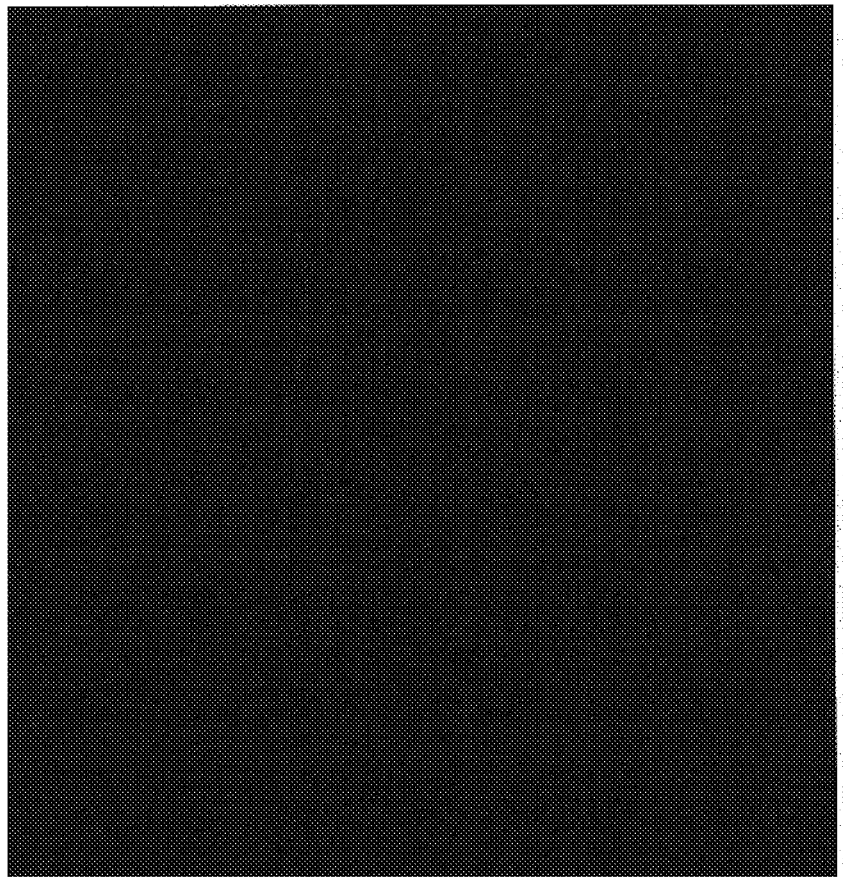
FIG. 7A is an image of a gel depicting a RT-PCR analysis of *C. pneumoniae* 16s rRNA gene expression in infected cultured keratinocytes. Normal human neonatal keratinocytes were infected with the laboratory strain of *C. pneumoniae* (TW-183) at 5000 IFU/50 cells. Following cell culture for 3 days in T-25 flasks, RNA was extracted from the cells and treated with DNase. cDNA was prepared from 1–2 micrograms of the treated RNA using MuLV reverse transcriptase. The cDNA was subjected to PCR using primers to the 16s rRNA gene of *C. pneumoniae*. The lanes depicted are as follows: lane 1, a DNA ladder; lane 2, cDNA from uninfected cells; lane 3, a PCR product for 16S rRNA gene from infected cells; and lane 4, DNA from TW-183 (i.e., the positive control).
Figure 7B:
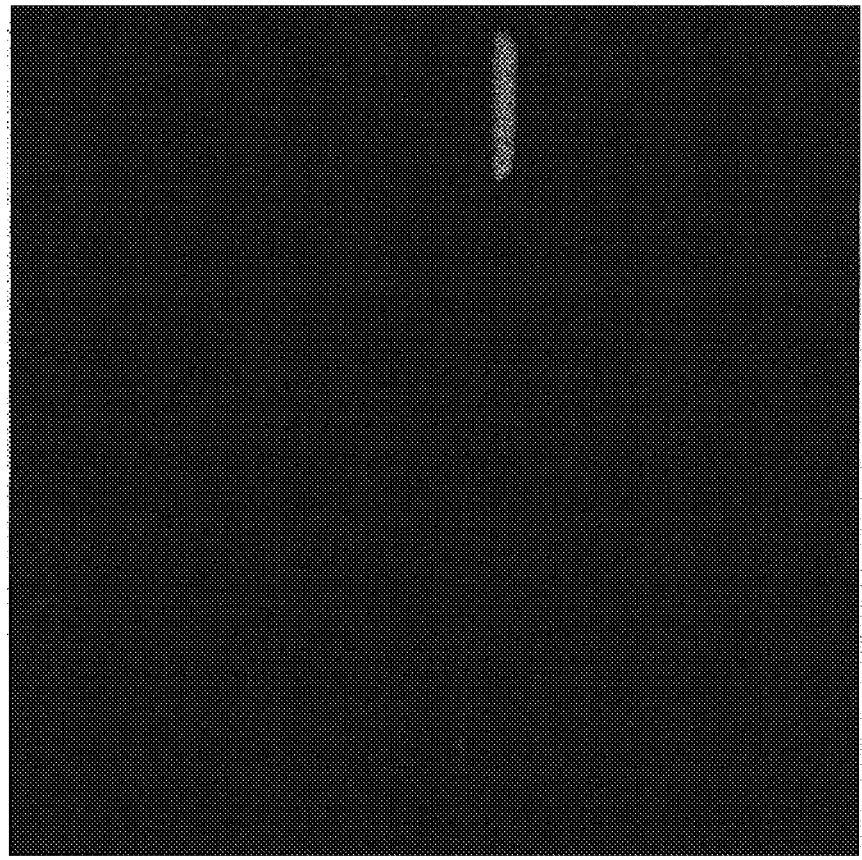
FIG. 7B is an image of a gel depicting an RT-PCR analysis of *C. pneumoniae* omp-A gene expression in infected cultured keratinocytes. Normal human neonatal keratinocytes were infected with the laboratory strain of *C. pneumoniae* (TW-183) at 5000 IFU/50 cells. Following cell culture for 3 days in T-25 flasks, RNA was extracted from the cells and treated with DNase. CDNA was prepared from 1–2 micrograms of the treated RNA using MuLV reverse transcriptase. The cDNA was subjected to PCR using primers to the omp-A gene (omp-A primer set 1, see Methods elsewhere herein). The lanes depicted are as follows: lane 1, a DNA ladder; lane 2, a cDNA from the uninfected culture; lane 3, a PCR product for the omp-A gene from the infected culture; and lane 4, a PCR product for omp-A gene from TW-183.
Figure 7C:
FIG. 7C is an image of a photomicrograph depicting keratinocytes infected with *C. pneumoniae* immunostained using anti-LPS. Keratinocytes in chamber slides were infected with *C. pneumoniae* (200 IFU/50 per cm$^2$ in 25 cm$^2$ flasks). After 3 days, the cells were washed and fixed with S.T.F.®, and exposed to anti-LPS. The bar indicates 50 micrometers.
Figure 7D:
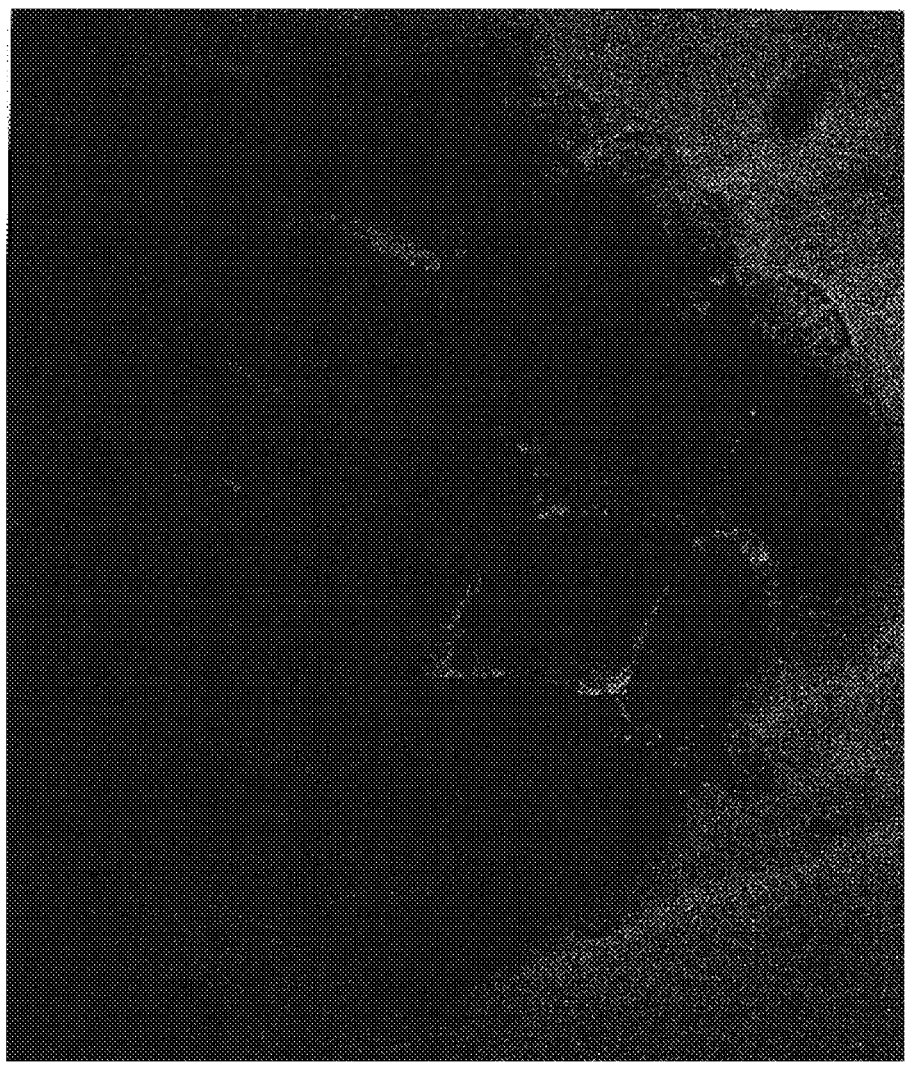
FIG. 7D is an image of a photomicrograph depicting keratinocytes infected with *C. pneumoniae* immunostained using anti-OMP. Keratinocytes in chamber slides were infected with *C. pneumoniae* (200 IFU/50 per cm$^2$ in 25 cm$^2$ flasks). After 3 days, the cells were washed and fixed with S.T.F.®, and exposed to anti-OMP. The bar indicates 50 micrometers.
Figure 7E:
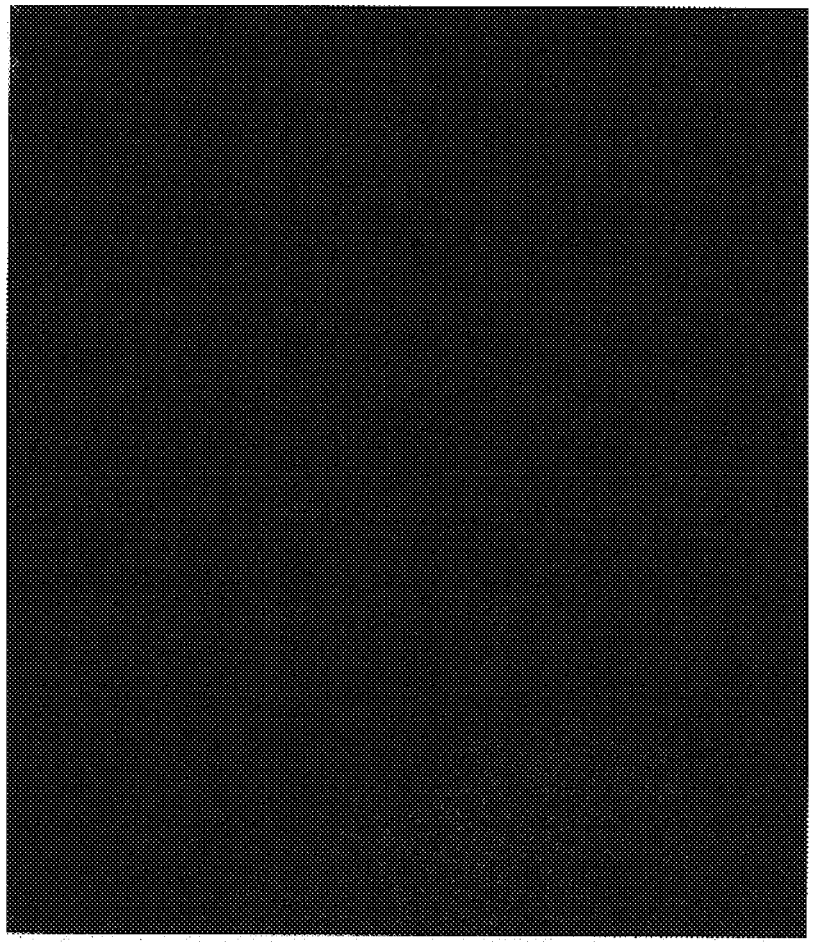
FIG. 7E is an image of a photomicrograph depicting control, uninfected keratinocytes immunostained using anti-LPS. Established uninfected keratinocytes in chamber were washed and fixed with S.T.F.®, and exposed to anti-LPS. The bar indicates 50 micrometers.
Figure 7F:
FIG. 7F is an image of a photomicrograph depicting uninfected keratinocytes immunostained using anti-OMP. Established, uninfected keratinocytes in chamber slides were washed and fixed with S.T.F.®, and exposed to anti-OMP. The bar indicates 50 micrometers.

Infection of C. pneumoniae in the epidermis has not been previously described. Thus, immunostaining of keratinocytes from CTCL patients with the anti-SAF and anti-OMP specific mAbs was intriguing. Although the data presented here are consistent with keratinocyte infection, it was necessary to determine to what extent the infection of keratinocytes with the laboratory strain of C. pneumoniae could be demonstrated. Normal human keratinocytes grown in T-25 flasks or in chamber slides were incubated for 3 days with 200 IFU/50 per $cm^2$ of TW-183. T-25 flasks were harvested and DNA and RNA were isolated and subjected to PCR or RT-PCR analysis using primers independent from those used on the biopsied samples to diminish the possibility of contamination. The chamber slides were fixed with S.T.F. and then stained with anti-OMP or LPS, as before. We observed that keratinocytes can be productively infected with C. pneumoniae. As shown in FIGS. 7A and 7B, RT-PCR results using 16s rRNA and omp-A primers were positive. In addition, LPS and OMP-positive organisms were found within the cultured keratinocytes using immunocytochemistry as depicted in FIGS. 7C and 7D, respectively. These data indicate that keratinocytes in vitro can be infected with C. pneumoniae, thereby supporting the observation of the immunolabelling of infected keratinocytes in the epidermis from CTCL patients in situ.

The results of the experiments presented in these Examples are now discussed with reference to possible mechanistic implications and practical applications.

Figure 8:
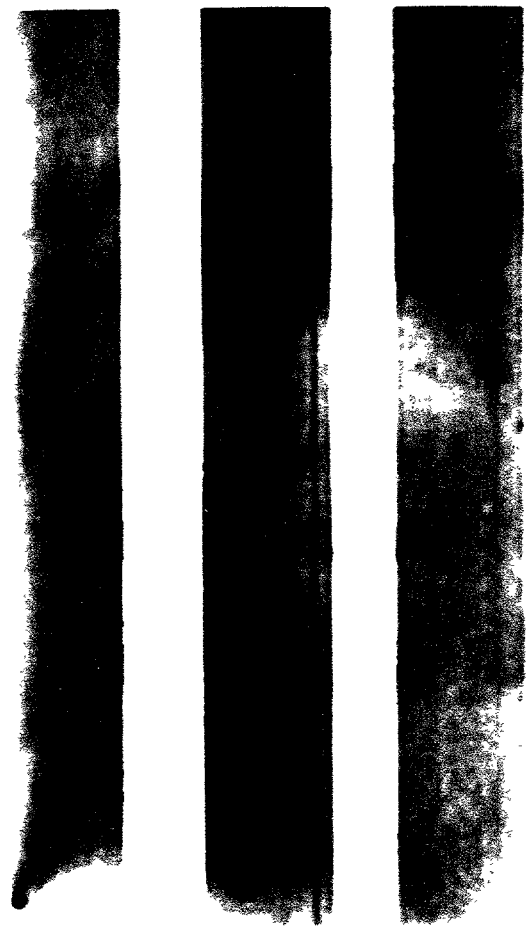
FIG. 8 depicts an immunoblot of anti-SAF reactivity to *C pneumoniae* proteins. Anti-SAF (1:100) (lanes 1–3) reactivity to lysates made with uninfected THP-1 cells (lane 1). *C. pneumoniae* from an AD brain (lane 2), and *C. pneumoniae* TW-183 from ATCC (lane 3). Proteins were electrophoresed, transferred to nitrocellulose, and tested for reactivity. Antibody binding was detected with anti-mouse conjugated with HRP. Secondary antibody binding was revealed by enhanced chemiluminescence and exposed to Hyperfilm-ECL for 10 minutes.

To confirm that AD isolated Chlamydia pneumoniae is associated with a 28–30 kDa protein as determined by SAF bioassay, we performed an immunoblot experiment. FIG. 8 depicts an immunoblot of anti-SAF reactivity to C pneumoniae proteins. Anti-SAF (1:100) (lanes 1–3) reactivity to lysates made with uninfected THP-1 cells (lane 1). C. pneumoniae from an AD brain (lane 2), and C. pneumoniae TW-183 from ATCC (lane 3). Proteins were electrophoresed, transferred to nitrocellulose and tested for reactivity. Antibody binding was detected with anti-mouse conjugated with HRP. Secondary antibody binding was revealed by enhanced chemiluminescence and exposed to Hyperfilm-ECL for 10 minutes. The blot demonstrates that anti-SAF reacts with a 28 kDa band in the lane prepared with proteins from Chlamydia pneumoniae isolated from an AD patient (FIG. 8, lane 2) that was also found to be SAF-positive in cell cultures (see FIG. 3C).

Discussion

Cell lines of malignant Sézary cells generated using a combination of SAF and irradiated allogeneic PBMC suggested that SAF may be an autocrine growth factor for these cells (Abrams et al., 1991, J. Immunol. 146:1455–1462). Since previous studies were restricted to patients with Sézary syndrome, it was necessary to determine whether SAF could be detected within the skin of patients suffering from mycosis fungoides, the predominant subset of CTCL. While the results indicating that SAF is present in the skin of patients with CTCL were striking, it was surprising that the SAF positive cells did not include infiltrating lymphocytes. Instead, SAF staining of endothelial cells, histiocytes, and keratinocytes was detected. These data suggest that SAF was present in vivo and found in cells resident to the skin rather than in the infiltrating lymphocytes. Without wishing to be bound by any particular theory, the identity of the SAF positive cells within the skin and the ability of SAF to stimulate malignant cell growth suggests that SAF could directly contribute to the pathogenesis of CTCL and potentially help explain the epidermotropism of this disease.

The decision to examine C. pneumoniae as the biologic source of SAF came about following the determination that SAF appeared to have a cell-associated form, and that this form of SAF was found to be complexed with RNA and DNA in the cytoplasm. These observations indicated that SAF could be associated with a large macromolecular complex. Originally, anti-SAF was found to be reactive intracellularly with the SZ-4 cell line, and was thought to be associated with a retrotransposon, but no evidence could be found to support this. For reasons not established at that point, the SZ-4 cell line over time lost its immunoreactivity and ability to produce soluble SAF. It is now considered that the use of antibiotics during routine passaging of the cultures may be the reason for loss of SAF activity.

Anti-OMP immunoreactivity was found in approximately 60% of the patients tested and overall there was nearly 90% concordance between anti-SAF, LPS, and anti-OMP staining. Negative results may relate to treatment received before evaluation, or to disease unrelated to the observed infection. OMP specific primers were found to amplify a 350 bp C. pneumoniae amplimer in both DNA and RNA preparations, supporting the immunohistochemical results. These data indicate that C. pneumoniae was present in the skin of many patients with CTCL. However, the question remained whether SAF was a chlamydial antigen or whether SAF was induced by C. pneumoniae infection. To address this issue, THP-1 monocyte cells were infected with C. pneumoniae isolates, and immunolabelled with anti-chlamydial reagents and anti-SAF. Striking results indicated clearly that SAF immunoreactivity was associated with the AD-isolated bacterium in these cultures, and also was expressed in inclusions in a diffuse pattern in TW-183-infected cultures. The small bodies that were not reactive with either antibody in the AD isolate appear to represent the infectious elementary bodies, or may be a persistent form of the bacteria that has been observed in other disorders (Koehler et al., 1997, Microbial Pathogenesis 22:133–42). To further confirm these studies, ultrastructural analysis using a combination of negative staining and immunoelectron microscopy indicated that anti-SAF labeled the AD isolated bacterium.

If SAF is a chlamydial protein, then protein extracts from the bacteria should contain specific bands reactive with the anti-SAF mAb. Immunoblotting with the anti-OMP and anti-SAF mAbs was performed, and indicated that anti-SAF reacted to the predicted 30 kDa SAF band. In addition, a few other higher molecular mass bands showed some reactivity with anti-SAF. However, because the identity of chlamydial antigens is still not complete, it can not fully be interpreted whether these bands represent forms of the SAF or cross-reactivity to homologous proteins. It is clear that anti-SAF, an antibody raised against a soluble factor, is reacting with protein bands made from lysates containing C. pneumoniae. Further experiments, however, would be required to clarify this issue.

An association between CTCL with an infection of cells resident to the epidermis is an attractive hypothesis. The fact that C. pneumoniae expresses heat shock proteins, LPS, and the SAF determinant, indicates that this bacterium certainly could induce a potent immune response resulting in lymphocytic infiltration of the skin. CTCL is a disease with a high degree of complexity whose pathogenesis is assuredly a result of multiple interactions. Without wishing to be bound by any particular theory, these interactions may include: the production of cytokines and chemokines by host skin cells, infiltrating non-malignant cells, and infiltrating malignant clonal T cells, in addition to the status of putative stimuli initiating the inflammatory process (Fermand et al., 1993, Brit. J. Haematol. 83:359–64).

Although the Th1/Th2 balance has not been directly studied in chlamydial responses, the induction of proinflammatory cytokines such as TNFα, IL-1β, IL-6, IFN-γ, and IFN-α suggests that a Th1 response would normally predominate (Halme and Surcel, 1997, Scand. J. Infect. Dis. Suppl. 104:18–21; Kaukoranta-Tolvanene et al., 1996, Microbial Pathogenesis 21:215–21; Simon et al., 1993, Clin. Exp. Immunol. 94:122–126). However, this may not be the case in elderly individuals or in the skin of patients with CTCL, and there is evidence indicating that chlamydial infections also can induce a Th2 response (Halme et al., 1997, Scand. J. Immunol. 45:378–384). The Th2-like cytokine pattern observed in CTCL lesions (Vowels et al., 1992, J. Investig. Dermatol. 99:90–4), may create a permissive environment for C. pneumoniae infection. This concept is supported by studies demonstrating that the skin of aged mice has been shown to be highly susceptible to infection by intracellular pathogens (Sunderkotter et al., 1997, Arch. Dermatol. 133:1256–1262). Although data in reactive arthritis generally support a Th1 response, Th2 activation in chlamydial immunity also is supported by production of IL-4 and IL-10 by *chlamydia*-specific T cell clones (Simon et al., 1993, Clin. Exp. Immunol. 94:122–126). In fact, detection of IL-10 is considered a sign of chronic C. pneumoniae infection (Kaukoranta-Tolvanene et al., 1996, Microbial Pathogenesis 21:215–21). Likewise, high concentrations of IFNγ and IFNα inhibit growth, but promote persistence of chlamydial infections purportedly by a lessening of exogenous tryptophan (Shener and Sarov, 1985, Current Microbiol. 16:9–13), thereby reducing the apparent infection. Thus, the relationship between increased CD8+ cells, and improved prognosis in CTCL might be explained by their IFN production rather then solely by the proposed increase in an anti-tumor cell mediated response (Wood et al., 1994, J. of Cutaneous Pathol. 21:151–6). Furthermore, the therapeutic value of IFNα in CTCL (Jorg et al., 1994, Dermatologic. Clinics. 12:433–41) could be attributed to the bacteriostatic effects of this cytokine (Shener and Sarov, 1985, Current Microbiol. 16:9–13).

Recent evidence demonstrating that C. pneumoniae is associated with inflammatory diseases throughout the body such as reactive arthritis (Gran et al., 1993, Scand. J. Rheumatol. 22:43–44), atherosclerosis (Campbell et al., 1995, J. Infect. Dis. 172:585–588), and Alzheimer's disease (Balin et al., 1998, Med. Micro. & Immunol. 187:23–42), further supports the surprising discovery disclosed herein that this bacterium is detected in the skin of patients with CTCL. Interestingly, the related species *C. trachomatis* has been shown to cause lymphomatus granulosum venereum, a disorder involving lymphoproliferation (Burgoyne et al., 1990, Primary Care: Clinics in Office Practice. 17:153–157), and shown to become systemic through infection of monocytes.

Studies have not yet been conducted to examine whether *C. pneumoniae* infection of the skin is common. In addition, under the correct permissive circumstances, many organisms that commonly infect humans can cause serious illness, for example group A *Streptococcus* and necrotizing fascitis (Lorber, 1996, Annals of Internal Med. 125:844–851). *C. pneumoniae* could reasonably contribute to the heterogeneity of inflammatory cells that infiltrate CTCL lesions (Fermand et al., 1993, Brit. J. Haematol. 83:359–64; Wood et al., 1994, J. Cutaneous Pathol. 21:151–6). In addition, this bacterium could induce the immunoregulatory events that occur during CTCL (Abrams et al., 1991, J. Immunol. 146:1455–1462; Hanson, 1996, Arch. Dermatol. 132:554–561), and the histologic changes that include the expression of HLA-DR (Wood et al., 1994, Internat. J. Dermatol. 33:346–50), consistent with a bacterial infection (Nickoloff et al., 1993, J. Dermatol. Science 6:127–33). Without wishing to be bound by any particular theory, the data disclosed herein and other studies (Jackow et al., 1997, Blood 89:32–40; Tan et al., 1974, British J. Dermatol. 91:607–616) suggest that chronic epidermal stimulation leads to clonal T cell expansion, followed by conversion of that clone to a malignant entity that can potentially lead to tumor development and in some cases, death of the patient.

The experiments presented in these Examples demonstrate that the biologically and biochemically characterized stimulatory factor, SAF, is present on *C. pneumoniae* organisms, that SAF and *C. pneumoniae* antigens are present in lesions of certain CTCL patients, and that DNA and RNA of *C. pneumoniae* can be detected in those CTCL patients. These experiments also demonstrate that following effective PUVA therapy, SAF and other *C. pneumoniae* antigens are greatly reduced within the skin, perhaps as a result of UV damage to the *C. pneumoniae* bacteria. Furthermore, experiments in vitro, demonstrated that keratinocytes were capable of being infected with *C. pneumoniae*, supporting the morphologic identification of the infected cells in situ. Without wishing to be bound by any particular theory, these data suggest that there is a causal or risk factor relationship between the observed infection and the pathogenesis of CTCL, based, e.g., on the fact that SAF is a *C. pneumoniae*-associated determinant These results show that the SAF determinant is associated with *C. pneumoniae* bacteria by immunohistochemistry, immuno-electron microscopy, and culture analysis. Reactivity of antibodies against an outer membrane protein of *C. pneumoniae* or against the lipopolysaccharide of *Chlamydiae* demonstrated that these determinants are co-expressed in 90% of the SAF positive samples. The presence of *C. pneumoniae* DNA and RNA in the skin has been confirmed by PCR and RT-PCR, and by sequence analysis of the PCR products. The expression of the *C. pneumoniae* antigens and SAF appears to be associated with active disease in that *C. pneumoniae* antigens were absent or greatly diminished in the skin of 3 patients examined post-Psoralen and UVA treatment. These results suggest that SAF is a *Chlamydia*-associated protein and suggest that SAF and *C. pneumoniae* may play a role in the pathogenesis of cutaneous T cell lymphomas.

The experiments presented in these Examples describe the following observations that have not been previously observed and that are necessary to understand the present invention:

1. Normal keratinocytes are capable of being productively infected with *C. pneumoniae* in culture using the well-characterized lab strain of *C. pneumoniae*, TWR 183.

2. The infection of keratinocytes by *C. pneumoniae* occurs in vivo.

3. Chlamydial LPS and the OMP of *C. pneumoniae* are detectable in keratinocytes and phagocytic cell types present in the skin of patients with CTCL. Many of these cells also contain RNA and DNA sequences derived from the ompA gene of *C. pneumoniae*.

4. SAF, the factor previously shown to induce functional IL-2 receptors on malignant T cells involved in the pathology associated with certain types of CTCL, is coexpressed with the chlamydial OMP and LPS in the lesions of patients with certain types of CTCL. SAF is also observed to be intimately associated with *C. pneumoniae* bacteria according to electron microscopic analysis.

5. The expression of SAF, the chlamydial LPS, and the *C. pneumoniae* OMP are expressed in patients with active CTCL and not in patients who have responded to therapy (i.e., PUVA).

6. A ten-day course of anti-chlamydial therapy was effective in ablating symptoms of mycosis fungoides, a form of CTCL, in at least one patient tested.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention.

What is claimed is:

1. A method of treating a *Chlamydia pneumoniae* infection in skin of a mammal having a cutaneous T-cell lymphoma, said method comprising:
   administering to said mammal, in amounts sufficient to treat said *Chlamydia pneumoniae* infection of said mammal having said cutaneous T-cell lymphoma, psoralen ultraviolet A (PUVA) in combination with at least one agent selected from the group consisting of fluoroquinolone, a macrolide, tetracycline, a tetracycline derivative, penicillin, and a penicillin derivative;
   and examining said mammal during and/or after said administering to monitor treatment of said *Chlamydia pneumoniae* infection.

2. The method of claim 1, wherein said mammal is a human.

3. A method of treating a cutaneous T-cell lymphoma in a mammal having a *Chlamydia pneumoniae* infection, said method comprising:
   administering to said mammal, in amounts sufficient to treat *Chlamydia pneumoniae* infection and thereby treating said cutaneous T-cell lymphoma, psoralen ultraviolet A (PUVA) in combination with at least one agent selected from the group consisting of fluoroquinolone, a macrolide, tetracycline, a tetracycline derivative, penicillin, and a penicillin derivative;
   examining said mammal during and/or after said administering to monitor treatment of said *Chlamydia pneumoniae* infection, thereby treating said cutaneous T-cell lymphoma.

4. The method of claim 3, wherein said mammal is a human.

5. The method of claim 3, wherein said cutaneous T-cell lymphoma is a member selected from the group consisting of mycosis fungoides, Sézary syndrome, lymphomatoid papillosis, Ki-1 lymphoma, exfoliative exematous rash, and digitate parapsoriasis.

6. The method of claim 3, wherein said *Chlamydia pneumoniae* infection is a member selected from the group consisting of a skin infection, a blood infection and a lymph node infection.

7. The method of claim 1, further comprising administering to said mammal at least one non-steroidal anti-inflammatory drug (NSAID).

8. The method of claim 1, wherein said examining comprises detecting Sezary T-cell activating factor (SAF) to monitor treatment of said *Chlamydia pneumoniae* infection.

9. The method of claim 3, further comprising administering to said mammal at least one non-steroidal anti-inflammatory drug (NSAID).

10. The method of claim 3, wherein said examining comprises detecting Sezary T-cell activating factor (SAF) to monitor treatment of said *Chlamydia pneumoniae* infection.

11. The method of claim 1, wherein the mammal is not vaccinated against *Chlamydia pneumoniae* infection.

12. The method of claim 3, wherein the mammal is not vaccinated against *Chlamydia pneumoniae* infection.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<221> NAME/KEY: Unsure
<222> LOCATION: (1)..(20)

<223> OTHER INFORMATION: MOMP Residues 281-300 Chlamydia pneumoniae

<400> SEQUENCE: 1
ctgcaaacta tactactgcc                                                    20

<210> SEQ ID NO 2
<211> LENGTH: 21
<212> TYPE: DNA
<213> ORGANISM: Artificial Sequence
<220> FEATURE:
<221> NAME/KEY: Unsure
<222> LOCATION: (1)..(21)
<223> OTHER INFORMATION: MOMP residues 1073- 1053 Chlamydia pneumoniae

<400> SEQUENCE: 2
cctacagtaa ctccacaagc t                                                  21

<210> SEQ ID NO 3
<211> LENGTH: 22
<212> TYPE: DNA
<213> ORGANISM: Artificial Sequence
<220> FEATURE:
<221> NAME/KEY: unsure
<222> LOCATION: (1)..(22)
<223> OTHER INFORMATION: MOMP residues 390-411 Chlamydia pneumoniae

<400> SEQUENCE: 3
tcgctttgat gttttctgta ct                                                 22

<210> SEQ ID NO 4
<211> LENGTH: 20
<212> TYPE: DNA
<213> ORGANISM: Artificial Sequence
<220> FEATURE:
<221> NAME/KEY: Unsure
<222> LOCATION: (1)..(20)
<223> OTHER INFORMATION: MOMP residues 730- 711 Chlamydia pneumoniae

<400> SEQUENCE: 4
aagcaacgcc tttatagccc                                                    20

<210> SEQ ID NO 5
<211> LENGTH: 20
<212> TYPE: DNA
<213> ORGANISM: Artificial Sequence
<220> FEATURE:
<221> NAME/KEY: Unsure
<222> LOCATION: (1)..(20)
<223> OTHER INFORMATION: 16s rRNA residues 71-90 Chlamydia pneumoniae

<400> SEQUENCE: 5
ataatgactt cggttgttat                                                    20

<210> SEQ ID NO 6
<211> LENGTH: 20
<212> TYPE: DNA
<213> ORGANISM: Artificial Sequence
<220> FEATURE:
<221> NAME/KEY: unsure
<222> LOCATION: (1)..(20)
<223> OTHER INFORMATION: 16s rRNA residues 1465-1446 C. pneumoniae

<400> SEQUENCE: 6
tataaatagg ttgagtcaac                                                    20

<210> SEQ ID NO 7
<211> LENGTH: 24

-continued

<212> TYPE: DNA
<213> ORGANISM: Artificial Sequence
<220> FEATURE:
<221> NAME/KEY: unsure
<222> LOCATION: (1)..(24)
<223> OTHER INFORMATION: 16s rRNA residues 243-266 Chlamydia pneumoniae

<400> SEQUENCE: 7
tatgcgatat cagcttgttg gtgg 24

<210> SEQ ID NO 8
<211> LENGTH: 24
<212> TYPE: DNA
<213> ORGANISM: Artificial Sequence
<220> FEATURE:
<221> NAME/KEY: unsure
<222> LOCATION: (1)..(24)
<223> OTHER INFORMATION: 16s rRNA residues 976-953 Chlamydia pneumoniae

<400> SEQUENCE: 8
gcatcgaatt aaaccacatg ctcc 24

<210> SEQ ID NO 9
<211> LENGTH: 18
<212> TYPE: DNA
<213> ORGANISM: Artificial Sequence
<220> FEATURE:
<221> NAME/KEY: unsure
<222> LOCATION: (1)..(18)
<223> OTHER INFORMATION: MOMP residues 26-43 Chlamydia pneumoniae

<400> SEQUENCE: 9
tattatccgc cgcatttg 18

<210> SEQ ID NO 10
<211> LENGTH: 20
<212> TYPE: DNA
<213> ORGANISM: Artificial Sequence
<220> FEATURE:
<221> NAME/KEY: unsure
<222> LOCATION: (1)..(20)
<223> OTHER INFORMATION: MOMP residues 567-548 Chlamydia pneumoniae

<400> SEQUENCE: 10
agagaaagag gtgtctgtgt 20

<210> SEQ ID NO 11
<211> LENGTH: 21
<212> TYPE: DNA
<213> ORGANISM: Artificial Sequence
<220> FEATURE:
<221> NAME/KEY: unsure
<222> LOCATION: (1)..(21)
<223> OTHER INFORMATION: MOMP residues 115-135 Chlamydia pneumoniae

<400> SEQUENCE: 11
acaatatggg agggtgctgc a 21

<210> SEQ ID NO 12
<211> LENGTH: 19
<212> TYPE: DNA
<213> ORGANISM: Artificial Sequence
<220> FEATURE:
<221> NAME/KEY: Unsure

```
-continued

<222> LOCATION: (1)..(19)
<223> OTHER INFORMATION: MOMP residues 462-444 Chlamydia pneumoniae

<400> SEQUENCE: 12
gagattgaac gctgtagag                                          19
```